United States Patent
Rauth et al.

(10) Patent No.: US 11,466,073 B2
(45) Date of Patent: Oct. 11, 2022

(54) HUMAN SERUM ALBUMIN VARIANTS AND USES THEREOF

(71) Applicant: CSL Limited, Parkville (AU)

(72) Inventors: Sabine Rauth, Parkville (AU); Andrew Hammet, Parkville (AU); Kirsten Edwards, Parkville (AU); Con Panousis, Parkville (AU)

(73) Assignee: CSL Limited, Parkville (AU)

( * ) Notice: Subject to any disclaimer, the term of this patent is extended or adjusted under 35 U.S.C. 154(b) by 59 days.

(21) Appl. No.: 16/640,562

(22) PCT Filed: Oct. 18, 2018

(86) PCT No.: PCT/AU2018/051131
§ 371 (c)(1),
(2) Date: Feb. 20, 2020

(87) PCT Pub. No.: WO2019/075519
PCT Pub. Date: Apr. 25, 2019

(65) Prior Publication Data
US 2020/0325209 A1    Oct. 15, 2020

(30) Foreign Application Priority Data
Oct. 18, 2017   (AU) ................................ 2017904211

(51) Int. Cl.
*C07K 14/765* (2006.01)
*A61K 47/64* (2017.01)
*A61K 38/00* (2006.01)

(52) U.S. Cl.
CPC .......... *C07K 14/765* (2013.01); *A61K 47/643* (2017.08)

(58) Field of Classification Search
CPC .................................................. C07K 14/176
See application file for complete search history.

(56) References Cited

U.S. PATENT DOCUMENTS

| | | | |
|---|---|---|---|
| 4,676,980 A | 6/1987 | Segal et al. | |
| 4,816,397 A | 3/1989 | Boss et al. | |
| 4,816,567 A | 3/1989 | Cabilly et al. | |
| 5,225,539 A | 7/1993 | Winter | |
| 5,463,564 A | 10/1995 | Agrafiotis et al. | |
| 5,565,332 A | 10/1996 | Hoogenboom et al. | |
| 5,585,089 A | 12/1996 | Queen et al. | |
| 5,731,168 A | 3/1998 | Carter et al. | |
| 5,807,715 A | 9/1998 | Morrison et al. | |
| 5,837,821 A | 11/1998 | Wu | |
| 6,054,297 A | 4/2000 | Carter et al. | |
| 6,113,898 A | 9/2000 | Anderson et al. | |
| 6,331,415 B1 | 12/2001 | Cabilly et al. | |
| 7,250,297 B1 | 7/2007 | Beste et al. | |
| 7,566,771 B1 | 7/2009 | Adair et al. | |
| 10,233,228 B2 * | 3/2019 | Plumridge | A61P 31/20 |
| 10,633,428 B2 * | 4/2020 | Delahay | A61K 47/643 |
| 2004/0132028 A1 | 7/2004 | Stumpp et al. | |
| 2007/0224633 A1 | 9/2007 | Skerra et al. | |
| 2008/0139791 A1 | 6/2008 | Lipovsek et al. | |
| 2014/0248682 A1* | 9/2014 | Gao | C07K 14/765 435/188 |
| 2014/0315817 A1* | 10/2014 | Schmidt | C07K 16/18 514/15.2 |

FOREIGN PATENT DOCUMENTS

| | | |
|---|---|---|
| EP | 0569141 A2 | 11/1993 |
| EP | 1641818 B1 | 12/2008 |
| WO | WO9404678 A1 | 3/1994 |
| WO | WO94/007921 A1 | 4/1994 |
| WO | WO9749805 A2 | 12/1997 |
| WO | WO98/044001 A1 | 10/1998 |
| WO | WO1999045110 A1 | 9/1999 |
| WO | WO2000034317 A2 | 6/2000 |
| WO | WO2001/079271 A1 | 10/2001 |
| WO | WO2002088171 A2 | 11/2002 |
| WO | WO2004108158 A1 | 12/2004 |
| WO | WO2005056764 A2 | 6/2005 |
| WO | WO2007/019620 A1 | 2/2007 |
| WO | WO2011/020866 A2 | 2/2011 |
| WO | WO2011/051489 A2 | 5/2011 |
| WO | WO2011/103076 A1 | 8/2011 |
| WO | WO2011107595 A1 | 9/2011 |

OTHER PUBLICATIONS

International Search Report dated Dec. 5, 2018 issued in PCT/AU2018/051131.

* cited by examiner

*Primary Examiner* — Manjunath N Rao
*Assistant Examiner* — Samuel W Liu
(74) *Attorney, Agent, or Firm* — Scully Scott Murphy and Presser

(57) ABSTRACT

A serum albumin variant, or functional fragment thereof, comprising one or more amino acid substitutions selected from (i) glycine, isoleucine, lysine, methionine, phenylalanine, tryptophan, tyrosine, valine and leucine substituted for glutamine at position (522); (ii) valine substituted for alanine at position (552); and (iii) alanine, glutamic acid, histidine, serine, lysine and arginine substituted for glycine at position (572).

6 Claims, 1 Drawing Sheet
Specification includes a Sequence Listing.

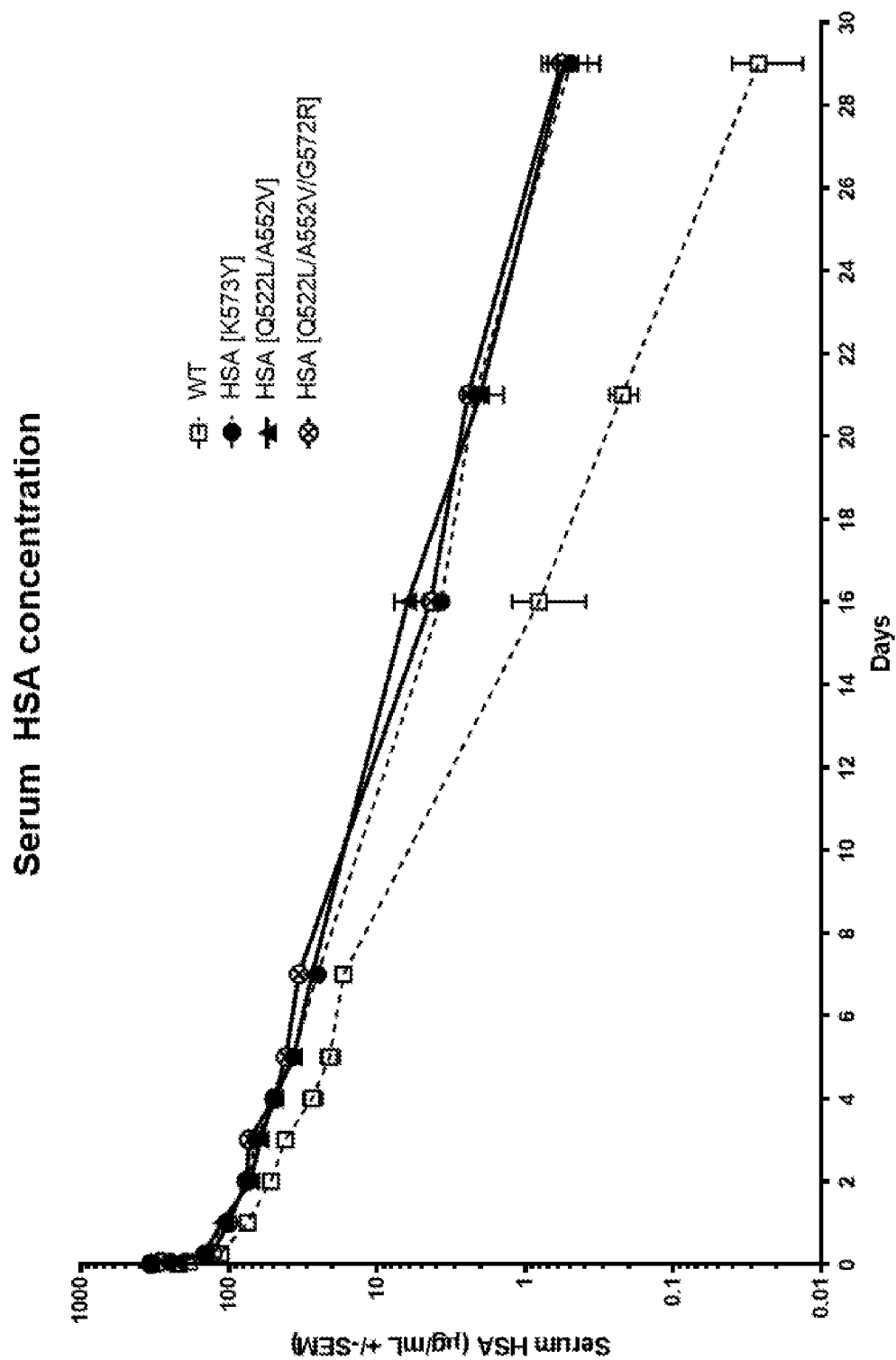

ional fragment thereof' filed 18 Oct. 2017. The
HUMAN SERUM ALBUMIN VARIANTS AND USES THEREOF

RELATED APPLICATION DATA

The present application claims priority from Australian Patent Application No. 2017904211 entitled 'Human serum albumin variant and uses thereof' filed 18 Oct. 2017. The entire contents of which is hereby incorporated by reference.

SEQUENCE LISTING

The present application is filed with a Sequence Listing in electronic form. The entire contents of the Sequence Listing are hereby incorporated by reference.

FIELD

The present disclosure relates to human serum albumin variants and uses thereof.

BACKGROUND

Serum albumin is the most abundant, naturally occurring protein in human plasma, with a major role in maintaining the osmotic pressure of blood, as well as in the transport of various substances in the blood stream.

Serum albumin is known to bind to a number of proteins in vivo, including the neonatal Fc receptor (FcRn) and this interaction is known to be important for the plasma half-life of albumin FcRn is a membrane bound protein, expressed in many cell and tissue types (e.g., endothelial cells), and is constantly being internalised and recycled. Albumin does not bind to FcRn at neutral pH but once endocytosed albumin binds to FcRn under the acidic conditions of the endosome. FcRn-bound albumin is rescued from degradation and is recycled back to the cell surface together with FcRn where, at physiological pH, it dissociates from FcRn.

Albumin has a long plasma half-life of approximately 19 days. This long half-life has led to the use of albumin to extend the half-life of pharmaceutical compounds. For example, albumin has been fused to human coagulation Factor IX (FIX) resulting in extended half-life of FIX (IDELVION®). Albumin has also been conjugated to chemotherapeutic compounds (such as paclitaxel) to increase drug half-life and drug accumulation (e.g., Abraxane®).

Human serum albumin variants having one or more amino acid substitutions that result in improved binding to or affinity for FcRn compared to natural serum albumin have been previously described (e.g., WO2011051489).

However, it will be clear to the skilled person that there is an on-going need in the art for serum albumin variants with improved pharmacokinetic properties, such as increased affinity for FcRn, increased plasma half-life and/or reduced clearance. There is also a need in the art to develop methods for controlling the plasma half-life of drugs in the plasma to optimize drug dosing and accumulation.

SUMMARY

The present disclosure is based on the inventors' identification that certain amino acid substitutions in serum albumin improve or increase its binding to the neonatal Fc receptor (FcRn). Serum albumin variants that have certain amino acid substitutions are capable of enhanced plasma half-life.

The inventors have determined that residues 522, 552 and 572 of SEQ ID NO: 1 are important for binding to the FcRn. Furthermore, the inventors have identified that substitution at these residues with certain amino acids increases or enhances binding to FcRn at acidic pH.

The findings by the inventors provide the basis for a serum albumin variant comprising one or more amino acid substitutions at a residue corresponding to amino acid 522, 552 or 572 of SEQ ID NO: 1. The findings by the inventors also provide the basis for methods for treating a disorder, e.g., a bleeding disorder in a subject.

The present disclosure provides, a serum albumin variant, or functional fragment thereof, comprising one or more amino acid substitutions selected from the group consisting of:
 (i) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1;
 (ii) valine substituted for alanine at a position corresponding to amino acid 552 of SEQ ID NO: 1;
 (iii) an amino acid selected from the group consisting of alanine, glutamic acid, histidine, serine, lysine and arginine substituted for glycine at a position corresponding to amino acid 572 of SEQ ID NO: 1; and
 (iv) combinations thereof.

In one example, the serum albumin variant, or functional fragment thereof, comprises an amino acid selected from the group consisting of glycine, isoleucine, lysine, methionine, phenylalanine, tryptophan, tyrosine, valine, and leucine substituted for glutamine at a position corresponding to amino acid 522 of SEQ ID NO: 1.

In one example, the serum albumin variant, or functional fragment thereof, comprises glycine substituted for glutamine at a position corresponding to amino acid 522 of SEQ ID NO: 1.

In one example, the serum albumin variant, or functional fragment thereof, comprises isoleucine substituted for glutamine at a position corresponding to amino acid 522 of SEQ ID NO: 1.

In one example, the serum albumin variant, or functional fragment thereof, comprises lysine substituted for glutamine at a position corresponding to amino acid 522 of SEQ ID NO: 1.

In one example, the serum albumin variant, or functional fragment thereof, comprises methionine substituted for glutamine at a position corresponding to amino acid 522 of SEQ ID NO: 1.

In one example, the serum albumin variant, or functional fragment thereof, comprises phenylalanine substituted for glutamine at a position corresponding to amino acid 522 of SEQ ID NO: 1.

In one example, the serum albumin variant, or functional fragment thereof, comprises tryptophan substituted for glutamine at a position corresponding to amino acid 522 of SEQ ID NO: 1.

In one example, the serum albumin variant, or functional fragment thereof, comprises tyrosine substituted for glutamine at a position corresponding to amino acid 522 of SEQ ID NO: 1.

In one example, the serum albumin variant, or functional fragment thereof, comprises valine substituted for glutamine at a position corresponding to amino acid 522 of SEQ ID NO: 1.

In one example, the serum albumin variant, or functional fragment thereof, comprises leucine substituted for glutamine at a position corresponding to amino acid 522 of SEQ ID NO: 1.

In one example, the serum albumin variant, or functional fragment thereof, comprises alanine substituted for glutamine at a position corresponding to amino acid 522 of SEQ ID NO: 1.

In one example, the serum albumin variant, or functional fragment thereof, comprises valine substituted for alanine at a position corresponding to amino acid 552 of SEQ ID NO: 1.

In one example, the serum albumin variant, or functional fragment thereof, comprises an amino acid selected from the group consisting of alanine, glutamic acid, histidine, serine, lysine and arginine substituted for glycine at a position corresponding to amino acid 572 of SEQ ID NO: 1.

In one example, the serum albumin variant, or functional fragment thereof, comprises alanine substituted for glycine at a position corresponding to amino acid 572 of SEQ ID NO: 1.

In one example, the serum albumin variant, or functional fragment thereof, comprises glutamic acid substituted for glycine at a position corresponding to amino acid 572 of SEQ ID NO: 1.

In one example, the serum albumin variant, or functional fragment thereof, comprises histidine substituted for glycine at a position corresponding to amino acid 572 of SEQ ID NO: 1.

In one example, the serum albumin variant, or functional fragment thereof, comprises serine substituted for glycine at a position corresponding to amino acid 572 of SEQ ID NO: 1.

In one example, the serum albumin variant, or functional fragment thereof, comprises lysine substituted for glycine at a position corresponding to amino acid 572 of SEQ ID NO: 1.

In one example, the serum albumin variant, or functional fragment thereof, comprises arginine substituted for glycine at a position corresponding to amino acid 572 of SEQ ID NO: 1.

In one example, the serum albumin variant, or functional fragment thereof, comprises valine substituted for glycine at a position corresponding to amino acid 572 of SEQ ID NO: 1.

In one example, the serum albumin variant, or functional fragment thereof, comprises an amino acid substitution as set out above at a position corresponding to amino acid 522 of SEQ ID NO: 1, amino acid 552 of SEQ ID NO: 1 and amino acid 572 of SEQ ID NO: 1.

In one example, the serum albumin variant, or functional fragment thereof, optionally comprises one or more amino acid substitutions, deletions or insertions in addition to an amino acid substitution as set out above at a position corresponding to amino acid 522 of SEQ ID NO: 1, amino acid 552 of SEQ ID NO: 1 and amino acid 572 of SEQ ID NO: 1. Additional amino acid substitutions suitable for use in the present disclosure will be apparent to the skilled person and include naturally-occurring substitutions and engineered substitutions such as those described, for example, in WO2011051489.

In one example, a serum albumin variant, or functional fragment thereof, of the present disclosure has improved pharmacokinetic properties compared to a serum albumin set forth in SEQ ID NO: 1. Pharmacokinetic properties of serum albumin will be apparent to the skilled person and include, for example, binding affinity to FcRn, plasma half-life and/or plasma clearance rate. Methods for determining pharmacokinetic properties of a serum albumin variant of the present disclosure will be apparent to the skilled person and/or described herein.

In one example, a serum albumin variant, or functional fragment thereof, of the present disclosure binds with increased affinity to FcRn compared to a serum albumin set forth in SEQ ID NO: 1. Methods for determining the affinity of the serum albumin variant, or functional fragment thereof, to FcRn will be apparent to the skilled person and/or described herein. In one example, the binding affinity of the serum albumin variant, or functional fragment thereof, for FcRn is determined by flow cytometry. For example, CHO cells stably expressing the serum albumin variant, or functional fragment thereof, are stained with alexa-488 labeled FcRn/β2m (to detect target binding) and anti-myc-alexa 647 (to detect expression) at acidic (pH 5.5) and neutral (pH 7.4) pH and analysed by flow cytometry. In one example, the affinity of the serum albumin variant, or functional fragment thereof, to FcRn/β2m is determined by calculating mean fluorescence intensity relative to an unmodified serum albumin (e.g., as set forth in SEQ ID NO: 1). In one example, the affinity of the serum albumin variant, or functional fragment thereof, is determined by biosensor analysis (e.g., using a surface plasmon resonance (SPR) assay). For example, the binding affinity (i.e., strength of interaction) of serum albumin variant, or functional fragment thereof, to immobilized FcRn is determined at pH 5.4 and/or pH 7.4 and 37° C. In another example, the binding affinity (i.e., strength of interaction) of immobilized serum albumin variant, or functional fragment thereof, to FcRn is determined at pH 5.4 and/or pH 7.4 and 37° C. In one example, the affinity constant ($K_D$), dissociation constant (Kd) and association constant (Ka) are determined. For example, the affinity constant ($K_D$) is the ratio of the dissociation constant (Kd) and association constant (Ka) (i.e., $K_D$=Kd/Ka).

In one example, the binding affinity is measured at acidic pH. For example, an acidic pH is a pH of less than about pH 6.0, such as about pH 5.9, or about pH 5.8, or about pH 5.7, or about pH 5.6, or about pH 5.5, or about pH 5.4, or about pH 5.3, or about pH 5.2, or about pH 5.1, or about pH 5.0. In one example, the serum albumin variant, or functional fragment thereof, of the present disclosure binds with increased affinity to FcRn at acidic pH compared to a serum albumin set forth in SEQ ID NO: 1. For example, the serum albumin variant, or functional fragment thereof, of the present disclosure binds with increased affinity to FcRn at lower pH, e.g., about pH 6.0, to facilitate binding in an endosome. In one example, the serum albumin variant, or functional fragment thereof binds with increased affinity to FcRn at about pH 6.0 compared to its affinity at about pH 7.4, which facilitates the re-release of the serum albumin variant into blood following cellular recycling. The amino acid substitutions of the present disclosure are useful for extending the half-life of the protein, by increasing FcRn-mediated recycling and thereby reducing clearance from the blood.

In one example, the level of binding of the serum albumin variant, or functional fragment thereof, of the present disclosure to FcRn is increased at pH 5.4 as determined by cell-binding studies compared to a serum albumin set forth in SEQ ID NO: 1. In one example, the level of binding of the serum albumin variant, or functional fragment thereof, of the present disclosure to FcRn is increased at pH 5.4 as determined by cell-binding studies compared to its affinity at pH 7.4. In one example, the level of binding of the serum albumin variant, or functional fragment thereof, of the present disclosure to FcRn is increased at pH 5.4 as determined by SPR analysis compared to its affinity at pH 7.4. In one example, the level of binding of the serum albumin variant, or functional fragment thereof, of the present disclosure to FcRn is increased at pH 5.4 as determined by flow cytometry compared to its affinity at pH 7.4.

In one example, the level of binding of the serum albumin variant, or functional fragment thereof, of the present disclosure to FcRn is increased by at least about 2 fold, or at least by about 4 fold, or at least by about 5 fold, or at least by about 10 fold, or at least by about 15 fold compared to a serum albumin set forth in SEQ ID NO: 1. In one example, the level of binding of the serum albumin variant to the FcRn is increased by about 2 fold to about 5 fold compared to a serum albumin set forth in SEQ ID NO: 1. For example, the level of binding of the serum albumin variant to the FcRn is increased by about 2 fold, or about 2.25 fold, or about 2.5 fold, or about 2.75 fold, or about 3 fold, or about 3.25 fold, or about 3.5 fold, or about 3.75 fold, or about 4 fold, or about 4.25 fold, or about 4.5 fold, or about 4.75 fold, or about 5 fold compared to a serum albumin set forth in SEQ ID NO: 1. In one example, the level of binding of the serum albumin variant to the FcRn is increased by about 2.4 fold, or about 2.8 fold, or about 3.1 fold, or about 3.4 fold, or about 3.7 fold, or about 3.9 fold, or about 4 fold, or about 4.8 fold compared to a serum albumin set forth in SEQ ID NO: 1.

In one example, the level of binding of the serum albumin variant to the FcRn is increased by about 5 fold to about 15 fold compared to a serum albumin set forth in SEQ ID NO: 1. For example, the level of binding of the serum albumin variant to the FcRn is increased by about 5 fold, or about 5.5 fold, or about 6 fold, or about 6.5 fold, or about 7 fold, or about 7.5 fold, or about 8 fold, or about 8.5 fold, or about 9 fold, or about 9.5 fold, or about 10 fold, or about 10.5 fold, or about 11 fold, or about 11.5 fold, or about 12 fold, or about 12.5 fold, or about 13 fold, or about 13.5 fold, or about 14 fold, or about 14.5 fold, or about 15 fold. In one example, the level of binding of the serum albumin variant to the FcRn is increased by about 7.6 fold, or about 8.6 fold, or about 13.8 fold compared to a serum albumin set forth in SEQ ID NO: 1.

In one example, the level of binding of the serum albumin variant to the FcRn is increased by about 15 fold to about 50 fold compared to a serum albumin set forth in SEQ ID NO: 1. For example, the level of binding of the serum albumin variant to the FcRn is increased by about 15 fold, or about 20 fold, or about 25 fold, or about 30 fold, or about 35 fold, or about 40 fold, or about 45 fold, or about 50 fold compared to a serum albumin set forth in SEQ ID NO: 1. In one example, the level of binding of the serum albumin variant to the FcRn is increased by about 42 fold, or about 43 fold, or about 47 fold, or about 48 fold compared to a serum albumin set forth in SEQ ID NO: 1.

In another example, the level of binding of the serum albumin variant to the FcRn is increased by about 50 to about 100 fold compared to a serum albumin set forth in SEQ ID NO: 1. For example, the level of binding of the serum albumin variant to the FcRn is increased by about 50 fold, or about 55 fold, or about 60 fold, or about 65 fold, or about 70 fold, or about 75 fold, or about 80 fold, or about 85 fold, or about 90 fold, or about 95 fold, or about 100 fold compared to a serum albumin set forth in SEQ ID NO: 1. In one example, the level of binding of the serum albumin variant to the FcRn is increased by about 57 fold, or about 58 fold compared to a serum albumin set forth in SEQ ID NO: 1.

In a further example, the level of binding of the serum albumin variant to the FcRn is increased by about 100 fold to about 250 fold compared to a serum albumin set forth in SEQ ID NO: 1. For example, the level of binding of the serum albumin variant to the FcRn is increased by about 100 fold, or about 110 fold, or about 120 fold, or about 130 fold, or about 140 fold, or about 150 fold, or about 160 fold, or about 170 fold, or about 180 fold, or about 190 fold, or about 200 fold, or about 210 fold, or about 220 fold, or about 230 fold, or about 240 fold, or about 250 fold compared to a serum albumin set forth in SEQ ID NO: 1. In one example, the level of binding of the serum albumin variant to the FcRn is increased by about 180 fold, or about 240 fold compared to a serum albumin set forth in SEQ ID NO: 1.

In one example, the level of binding of the serum albumin variant to the FcRn is increased by at least 250 fold compared to a serum albumin set forth in SEQ ID NO: 1. For example, the level of binding of the serum albumin variant to the FcRn is increased by about 200 fold, or about 250 fold, or about 300 fold, or about 350 fold, or about 400 fold, or about 450 fold, or about 500 fold compared to a serum albumin set forth in SEQ ID NO: 1. In one example, the level of binding of the serum albumin variant to the FcRn is increased by about 410 fold compared to a serum albumin set forth in SEQ ID NO: 1.

In one example, serum half-life of the serum albumin variant is increased compared to a serum albumin set forth in SEQ ID NO: 1. For example, the serum half-life of a serum albumin variant of the present disclosure is increased by at least about 1.5 fold compared to a serum albumin set forth in SEQ ID NO: 1. In one example, the serum half-life of a serum albumin variant of the present disclosure is increased by about 1.5 fold, or about 2 fold, or about 2.5 fold, or about 3 fold, or about 3.5 fold, or about 4 fold, or about 4.5 fold, or about 5 fold, or about 5.5 fold, or about 6 fold, or about 6.5 fold, or about 7 fold, or about 7.5 fold, or about 8 fold, or about 8.5 fold, or about 9 fold, or about 9.5 fold, or about 10 fold. In one example, the serum half-life of a serum albumin variant of the present disclosure is increased by about 5 days to about 10 days or more. For example, the serum half-life of a serum albumin variant of the present disclosure is increased by about 5 days, or about 6 days, or about 7 days, or about 8 days, or about 9 days, or about 10 days, or about 11 days, or about 12 days, or about 13 days, or about 14 days, or about 15 days, or about 16 days, or about 17 days, or about 18 days, or about 19 days, or about 20 days, or about 25 days, or about 30 days, or about 35 days, or about 40 days, or about 45 days, or about 50 days. Methods for determining the half-life of the serum albumin variant will be apparent to the skilled person and/or described herein. In one example, the half-life of the serum albumin variant is determined using an in vivo assay. In one example, the serum albumin concentration is measured in an Enzyme-Linked Immunosorbent Assay (ELISA) using human serum albumin specific antibodies. For example, the ELISA is performed using commercially available methods. In another example, serum albumin variant is injected intravenously into mice or cynomolgus monkeys and the plasma concentration is periodically measured as a function of time. In one example, the plasma concentration of serum albumin variant is measured at 3 minutes to 72 hours after the injection. In one example, the plasma concentration of serum albumin variant is measured up to 60 days after the injection. In one example, the serum albumin variant is radiolabelled. In one example, the in vivo half-life of the serum albumin variant, or functional fragment thereof, is determined by calculating the clearance rate in beta-phase.

In one example, the in vivo half-life of the serum albumin variant, or functional fragment thereof is compared to the in vivo half-life of unmodified serum albumin (e.g., as set forth in SEQ ID NO: 1).

In one example, the rate of clearance (i.e., recycling and uptake) of the serum albumin variant is decreased compared to a serum albumin set forth in SEQ ID NO: 1. Methods for determining the rate of clearance (i.e., recycling and uptake) of the serum albumin variant will be apparent to the skilled person and/or described herein. In one example, confocal fluorescence microscopy is used to determine if the serum albumin variant is recycled. For example, to determine if a serum albumin variant is recycled, fluorescently labelled serum albumin variant is incubated with cells expressing human FcRn receptor on the cell surface and visualised by confocal fluorescence microscopy.

In one example, a serum albumin variant, or functional fragment thereof, of the present disclosure comprises:
  (i) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, and valine substituted for alanine at position 552 of SEQ ID NO: 1; or
  (ii) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, and an amino acid selected from the group consisting of alanine, glutamic acid, histidine, serine, lysine and arginine substituted for glycine at position 572 of SEQ ID NO: 1; or
  (iii) valine substituted for alanine at a position corresponding to amino acid 552 of SEQ ID NO: 1, and an amino acid selected from the group consisting of alanine, glutamic acid, histidine, serine, lysine and arginine substituted for glycine at position 572 of SEQ ID NO: 1; or
  (iv) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, valine substituted for alanine at position 552 of SEQ ID NO: 1, and an amino acid selected from the group consisting of alanine, glutamic acid, histidine, serine, lysine and arginine substituted for glycine at position 572 of SEQ ID NO: 1.

In one example, a serum albumin variant, or functional fragment thereof, of the present disclosure comprises an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, and valine substituted for alanine at position 552 of SEQ ID NO: 1.

In one example, a serum albumin variant, or functional fragment thereof, of the present disclosure comprises an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, and an amino acid selected from the group consisting of alanine, glutamic acid, histidine, serine, lysine and arginine substituted for glycine at position 572 of SEQ ID NO: 1.

In one example, a serum albumin variant, or functional fragment thereof, of the present disclosure comprises valine substituted for alanine at a position corresponding to amino acid 552 of SEQ ID NO: 1, and an amino acid selected from the group consisting of alanine, glutamic acid, histidine, serine, lysine and arginine substituted for glycine at position 572 of SEQ ID NO: 1.

In one example, a serum albumin variant, or functional fragment thereof, of the present disclosure comprises an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, valine substituted for alanine at position 552 of SEQ ID NO: 1, and an amino acid selected from the group consisting of alanine, glutamic acid, histidine, serine, lysine and arginine substituted for glycine at position 572 of SEQ ID NO: 1.

In one example, a serum albumin variant, or functional fragment thereof, of the present disclosure additionally comprises tyrosine substituted for lysine at a position corresponding to amino acid 573 of SEQ ID NO: 1.

In one example, a serum albumin variant, or functional fragment thereof, comprises an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, and tyrosine substituted for lysine at a position corresponding to amino acid 573 of SEQ ID NO: 1.

In one example, a serum albumin variant, or functional fragment thereof, comprises valine substituted for alanine at a position corresponding to amino acid 552 of SEQ ID NO: 1, and tyrosine substituted for lysine at a position corresponding to amino acid 573 of SEQ ID NO: 1.

In one example, a serum albumin variant, or functional fragment thereof, comprises an amino acid selected from the group consisting of alanine, glutamic acid, histidine, serine, lysine and arginine substituted for glycine at a position corresponding to amino acid 572 of SEQ ID NO: 1, and tyrosine substituted for lysine at a position corresponding to amino acid 573 of SEQ ID NO: 1.

In one example, a serum albumin variant, or functional fragment thereof, of the present disclosure comprises an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, valine substituted for alanine at position 552 of SEQ ID NO: 1, and tyrosine substituted for lysine at a position corresponding to amino acid 573 of SEQ ID NO: 1.

In one example, a serum albumin variant, or functional fragment thereof, of the present disclosure comprises an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, an amino acid selected from the group consisting of alanine, glutamic acid, histidine, serine, lysine and arginine substituted for glycine at position 572 of SEQ ID NO: 1, and tyrosine substituted for lysine at a position corresponding to amino acid 573 of SEQ ID NO: 1.

In one example, a serum albumin variant, or functional fragment thereof, of the present disclosure comprises valine substituted for alanine at a position corresponding to amino acid 552 of SEQ ID NO: 1, an amino acid selected from the group consisting of alanine, glutamic acid, histidine, serine, lysine and arginine substituted for glycine at position 572 of SEQ ID NO: 1, and tyrosine substituted for lysine at a position corresponding to amino acid 573 of SEQ ID NO: 1.

In one example, a serum albumin variant, or functional fragment thereof, of the present disclosure comprises an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, valine substituted for alanine at position 552 of SEQ ID NO: 1, an amino acid selected from the group consisting of alanine, glutamic acid, histidine, serine, lysine and arginine substituted for glycine at position 572 of SEQ ID NO: 1, and tyrosine substituted for lysine at a position corresponding to amino acid 573 of SEQ ID NO: 1.

In one example, a serum albumin variant, or functional fragment thereof, of the present disclosure comprises:
  (i) leucine substituted for glutamine at a position corresponding to amino acid 522 of SEQ ID NO: 1; and/or
  (ii) valine substituted for alanine at a position corresponding to amino acid 552 of SEQ ID NO: 1; and/or
  (iii) arginine substituted for glycine at a position corresponding to amino acid 572 of SEQ ID NO: 1.

In one example, a serum albumin variant, or functional fragment thereof, of the present disclosure comprises leucine substituted for glutamine at a position corresponding to amino acid 522 of SEQ ID NO: 1.

In one example, a serum albumin variant, or functional fragment thereof, of the present disclosure comprises valine substituted for alanine at a position corresponding to amino acid 552 of SEQ ID NO: 1.

In one example, a serum albumin variant, or functional fragment thereof, of the present disclosure comprises arginine substituted for glycine at a position corresponding to amino acid 572 of SEQ ID NO: 1.

In one example, a serum albumin variant, or functional fragment thereof, of the present disclosure comprises:
  (i) leucine substituted for glutamine at a position corresponding to amino acid 522 of SEQ ID NO: 1, and arginine substituted for glycine at a position corresponding to amino acid 572 of SEQ ID NO: 1; or
  (ii) leucine substituted for glutamine at a position corresponding to amino acid 522 of SEQ ID NO: 1, and valine substituted for alanine at a position corresponding to amino acid 552 of SEQ ID NO: 1; or
  (iii) valine substituted for alanine at a position corresponding to amino acid 552 of SEQ ID NO: 1, and arginine substituted for glycine at a position corresponding to amino acid 572 of SEQ ID NO: 1; or
  (iv) leucine substituted for glutamine at a position corresponding to amino acid 522 of SEQ ID NO: 1, and tyrosine substituted for lysine at a position corresponding to amino acid 573 of SEQ ID NO: 1; or
  (v) valine substituted for alanine at a position corresponding to amino acid 552 of SEQ ID NO: 1, and tyrosine substituted for lysine at a position corresponding to amino acid 573 of SEQ ID NO: 1; or
  (vi) arginine substituted for glycine at a position corresponding to amino acid 572 of SEQ ID NO: 1, and tyrosine substituted for lysine at a position corresponding to amino acid 573 of SEQ ID NO: 1; or
  (vii) leucine substituted for glutamine at a position corresponding to amino acid 522 of SEQ ID NO: 1, valine substituted for alanine at a position corresponding to amino acid 552 of SEQ ID NO: 1, and arginine substituted for glycine at a position corresponding to amino acid 572 of SEQ ID NO: 1; or
  (viii) leucine substituted for glutamine at a position corresponding to amino acid 522 of SEQ ID NO: 1, valine substituted for alanine at a position corresponding to amino acid 552 of SEQ ID NO: 1, and tyrosine substituted for lysine at a position corresponding to amino acid 573 of SEQ ID NO: 1; or
  (ix) leucine substituted for glutamine at a position corresponding to amino acid 522 of SEQ ID NO: 1, arginine substituted for glycine at a position corresponding to amino acid 572 of SEQ ID NO: 1, and tyrosine substituted for lysine at a position corresponding to amino acid 573 of SEQ ID NO: 1; or
  (x) leucine substituted for glutamine at a position corresponding to amino acid 522 of SEQ ID NO: 1, valine substituted for alanine at position 552 of SEQ ID NO: 1, arginine substituted for glycine at a position corresponding to amino acid 572 of SEQ ID NO: 1, and tyrosine substituted for lysine at a position corresponding to amino acid 573 of SEQ ID NO: 1.

In one example, a serum albumin variant, or functional fragment thereof, of the present disclosure comprises leucine substituted for glutamine at a position corresponding to amino acid 522 of SEQ ID NO: 1, and arginine substituted for glycine at a position corresponding to amino acid 572 of SEQ ID NO: 1.

In one example, a serum albumin variant, or functional fragment thereof, of the present disclosure comprises leucine substituted for glutamine at a position corresponding to amino acid 522 of SEQ ID NO: 1, and valine substituted for alanine at a position corresponding to amino acid 552 of SEQ ID NO: 1.

In one example, a serum albumin variant, or functional fragment thereof, of the present disclosure comprises valine substituted for alanine at a position corresponding to amino acid 552 of SEQ ID NO: 1, and arginine substituted for glycine at a position corresponding to amino acid 572 of SEQ ID NO: 1.

In one example, a serum albumin variant, or functional fragment thereof, of the present disclosure comprises leucine substituted for glutamine at a position corresponding to amino acid 522 of SEQ ID NO: 1, and tyrosine substituted for lysine at a position corresponding to amino acid 573 of SEQ ID NO: 1.

In one example, a serum albumin variant, or functional fragment thereof, of the present disclosure comprises valine substituted for alanine at a position corresponding to amino acid 552 of SEQ ID NO: 1, and tyrosine substituted for lysine at a position corresponding to amino acid 573 of SEQ ID NO: 1.

In one example, a serum albumin variant, or functional fragment thereof, of the present disclosure comprises arginine substituted for glycine at a position corresponding to amino acid 572 of SEQ ID NO: 1, and tyrosine substituted for lysine at a position corresponding to amino acid 573 of SEQ ID NO: 1.

In one example, a serum albumin variant, or functional fragment thereof, of the present disclosure comprises leucine substituted for glutamine at a position corresponding to amino acid 522 of SEQ ID NO: 1, valine substituted for alanine at a position corresponding to amino acid 552 of SEQ ID NO: 1, and arginine substituted for glycine at a position corresponding to amino acid 572 of SEQ ID NO: 1.

In one example, a serum albumin variant, or functional fragment thereof, of the present disclosure comprises leucine substituted for glutamine at a position corresponding to amino acid 522 of SEQ ID NO: 1, valine substituted for alanine at a position corresponding to amino acid 552 of SEQ ID NO: 1, and tyrosine substituted for lysine at a position corresponding to amino acid 573 of SEQ ID NO: 1.

In one example, a serum albumin variant, or functional fragment thereof, of the present disclosure comprises leucine substituted for glutamine at a position corresponding to amino acid 522 of SEQ ID NO: 1, arginine substituted for glycine at a position corresponding to amino acid 572 of SEQ ID NO: 1, and tyrosine substituted for lysine at a position corresponding to amino acid 573 of SEQ ID NO: 1.

In one example, a serum albumin variant, or functional fragment thereof, of the present disclosure comprises leucine substituted for glutamine at a position corresponding to amino acid 522 of SEQ ID NO: 1, valine substituted for alanine at position 552 of SEQ ID NO: 1, arginine substituted for glycine at a position corresponding to amino acid 572 of SEQ ID NO: 1, and tyrosine substituted for lysine at a position corresponding to amino acid 573 of SEQ ID NO: 1.

The present disclosure provides a serum albumin conjugate comprising the serum albumin variant, or functional fragment thereof, according to the present disclosure, and a compound.

In one example, a serum albumin conjugate of the present disclosure has a longer serum half-life compared to a serum albumin conjugate comprising a serum albumin set forth in SEQ ID NO: 1. Examples of increased serum half-life and assays for determining serum half-life are described herein and are to be taken to apply mutatis mutandis to this example of the disclosure.

In another example, a serum albumin conjugate of the present disclosure has an increased binding affinity for FcRn compared to a serum albumin conjugate comprising a serum albumin set forth in SEQ ID NO: 1. For example, the level of binding of the serum albumin conjugate to FcRn is increased by at least about 2 fold or 4 fold or 5 fold or 10 fold. For example, the level of binding to the FcRn is increased by at least about 2 fold or 10 fold or 40 fold or 100 fold or 150 fold. Examples of increased binding affinity for FcRn and assays for determining same are described herein and are to be taken to apply mutatis mutandis to this example of the disclosure.

In one example, the serum albumin variant, or functional fragment thereof, is conjugated to another compound and/or encapsulates another compound. Compounds contemplated by the present disclosure can take any of a variety of forms including natural compounds, chemical small molecule compounds or biological compounds.

In one example, the serum albumin variant, or functional fragment thereof, of the present disclosure is conjugated to a compound, which is directly or indirectly bound to the serum albumin variant, or functional fragment thereof.

Exemplary compounds include a protein, a protein comprising an antibody variable region, an antibody mimetic, a domain antibody, a toxin, a radioisotope, a detectable label, a peptide, a polypeptide, a colloid, a chemotherapeutic agent, a nucleic acid, a small molecule, antisense oligonucleotide, a short hairpin RNA (shRNA), a siRNA, an interfering RNA (RNAi), a ribozyme, a microRNA, a microRNA adapted shRNA (shRNAmir), a DNAzyme and mixtures thereof. In one example, the detectable label is an imaging agent.

In one example, the compound is a protein-based compound, e.g., a peptide, polypeptide or protein. In one example, the protein is a therapeutic protein.

In another example, the compound is a protein (e.g., a therapeutic protein) comprising a non-antibody antigen binding domain, such as an adnectin, an affibody, an atrimer, an evasin, a designed ankyrin-repeat protein (DARPin) or an anticalin.

In one example, the compound is a protein (e.g., a therapeutic protein) comprising a variable region fragment (Fv). For example, the protein is selected from the group consisting of:
(i) a single chain Fv fragment (scFv);
(ii) a dimeric scFv (di-scFv); or
(iii) a diabody;
(iv) a triabody;
(v) a tetrabody;
(vi) a Fab;
(vii) a F(ab')$_2$;
(viii) a Fv; or
(ix) one of (i) to (viii) linked to a constant region of an antibody, Fc or a heavy chain constant domain ($C_H$) 2 and/or $C_H$3.

In one example, the protein is an antibody or antigen binding fragment.

In one example, an antibody or antigen binding fragment of the present disclosure is recombinant, chimeric, CDR grafted, humanized, synhumanized, primatized, deimmunized or human.

In one example, the present disclosure provides a serum albumin variant, or functional fragment thereof, conjugated to a von Willebrand factor, or modified form thereof. For example, the compound is a von Willebrand factor, or a modified form thereof. In one example, the von Willebrand factor comprises a D'D3 domain.

In one example, the present disclosure provides a serum albumin variant, or functional fragment thereof, conjugated to a complement inhibitor or modified form thereof. For example, the compound is a complement inhibitor, or a modified form thereof. In one example, the complement inhibitor is selected from the group consisting of Factor I, (fI), Factor H (fH), C4b-binding protein (C4 bp), soluble CD55 (decay accelerating factor (DAF)), C1-inhibitor (C1-INH or C1 esterase inhibitor); soluble CD35 (sCR1); soluble CD46 (membrane cofactor protein (MCP)), soluble CD59 (protectin), TT30 (CR2-fH), Cobra venom factor (CVF) and a functional fragment or variant thereof.

In one example, the complement inhibitor is a soluble complement inhibitor, such as sCR1, or a functional fragment or variant thereof. In one example, the complement inhibitor is a variant or modified sCR1.

In one example, the complement inhibitor is a C1-inhibitor (i.e., C1-INH), or a functional fragment or variant thereof. In one example, the complement inhibitor is a variant of modified C1-INH.

In one example, the present disclosure provides a serum albumin variant, or functional fragment thereof, conjugated to a blood coagulation factor.

In another example, the present disclosure provides a serum albumin variant, or functional fragment thereof, conjugated to a compound that binds a blood coagulation factor. For example, the compound is or binds to a blood coagulation factor.

In one example, the blood coagulation factor is selected from the group consisting of Factor I, Factor II (prothrombin)/thrombin, Factor III, Factor V, Factor VII, Factor VIII, Factor IX, Factor X, Factor XI, Factor XII Factor XIII and an activated form of any of the foregoing. For example, the blood coagulation factor is Factor IX and/or Factor IXa. In another example, the blood coagulation factor is Factor X and/or Factor Xa. In a further example, the blood coagulation factor is Factor IX/IXa and Factor X/Xa. In one example, the blood coagulation factor is Factor VII and/or Factor VIIa. In another example, the blood coagulation factor is Factor VIII and/or Factor VIIa.

The present disclosure also provides a composition comprising a serum albumin conjugate of the disclosure and a pharmaceutical carrier and/or excipient.

In one example, the composition has increased binding affinity for FcRn compared to a composition comprising a serum albumin conjugate comprising a serum albumin comprising a sequence set forth in SEQ ID NO: 1.

In one example, the composition has increased serum half-life compared to a composition comprising a serum albumin conjugate comprising a serum albumin comprising a sequence set forth in SEQ ID NO: 1.

The present disclosure also provides a method of treating or preventing a disease or condition in a subject, the method comprising administering the serum albumin conjugate of the present disclosure, or the composition comprising the serum albumin variant, or functional fragment thereof. In one example, the subject is in need thereof.

In one example, the present disclosure provides a serum albumin variant, or functional fragment thereof, or a serum albumin conjugate, or a composition comprising the serum albumin variant or functional fragment thereof, for use in treating or preventing a disease or condition in a subject.

In one example, the present disclosure provides use of the serum albumin conjugate of the present disclosure, or the composition comprising the serum albumin variant, or functional fragment thereof, of the present disclosure, in the manufacture of a medicament for the treatment or prevention of a disease or condition in a subject.

In one example, the disease or condition is a bleeding disorder.

In one example, the subject suffers from a bleeding disorder. In one example, the subject has been diagnosed as suffering from a bleeding disorder. In one example, the subject is receiving treatment for a bleeding disorder.

In one example of any method described herein, the serum albumin conjugate or composition comprising the serum albumin variant of the present disclosure is administered before or after the development of a bleeding disorder. In one example of any method described herein, the serum albumin conjugate or composition comprising the serum albumin variant of the present disclosure is administered before the development of the bleeding disorder. In one example of any method described herein, the serum albumin conjugate or composition comprising the serum albumin variant of the present disclosure is administered after the development of the bleeding disorder.

In one example of any method described herein, the serum albumin conjugate or composition comprising the serum albumin variant of the present disclosure is administered before or after the onset of a bleeding event. In one example, the serum albumin conjugate or composition comprising the serum albumin variant of the present disclosure is administered before the onset of a bleeding event. In another example, the serum albumin conjugate or composition comprising the serum albumin variant of the present disclosure is administered after the onset of a bleeding event.

A bleeding event will be apparent to the skilled person and include, for example a minor and/or major bleeding event. In one example, the bleeding event is a major bleeding event. For example, a major bleeding event is any episode of bleeding that leads to $\geq 5$ g/dL reduced haemoglobin or a $\geq 15\%$ absolute decrease in haematocrit. In one example, the bleeding event is a minor bleeding event. For example, a minor bleeding event is any episode of bleeding that leads to $\leq 4$ g/dL reduced haemoglobin or a $\geq 10\%$ absolute decrease in haematocrit.

In one example, the subject is at risk of developing a bleeding disorder. For example, a subject at risk of developing a bleeding disorder includes, but is not limited to, those with a mutation, deletion or rearrangement in a blood coagulation factor, e.g., Factor VII and/or Factor IX, or those with a platelet disorder. In one example, the subject has a relative that has developed a bleeding disorder. For example, the bleeding disorder is inherited. In one example, the bleeding disorder is acquired.

In one example, the serum albumin conjugate or composition comprising the serum albumin variant is administered before or after the onset of symptoms of a bleeding disorder. In one example, the serum albumin conjugate or composition comprising the serum albumin variant is administered before the onset of symptoms of a bleeding disorder. In one example, the serum albumin conjugate or composition comprising the serum albumin variant is administered after the onset of symptoms of a bleeding disorder. In one example, the serum albumin conjugate or composition comprising the serum albumin variant of the present disclosure is administered at a dose that alleviates or reduces one or more of the symptoms of a bleeding disorder.

Symptoms of a bleeding disorder will be apparent to the skilled person and include, for example:

Easy bruising;
Bleeding gums;
Heavy bleeding from small cuts or dental work;
Unexplained nosebleeds;
Heavy menstrual bleeding;
Bleeding into joints; and/or
Excessive bleeding following surgery.

In one example, the bleeding disorder is caused by a blood coagulation disorder. For example, the blood coagulation disorder is haemophilia, von Willebrand disease, Factor I deficiency, Factor II deficiency, Factor V deficiency, combined Factor V/Factor VIII deficiency, Factor VII deficiency, Factor X deficiency, Factor XI deficiency or Factor XIII deficiency. In one example, the haemophilia is haemophilia A or haemophilia B. In one example, the subject has a condition requiring prophylactic treatment.

In one example, the serum albumin conjugate or composition comprising the serum albumin variant of the present disclosure is administered to the subject in an amount to reduce the severity of the bleeding in the subject.

In one example of any method described herein, the subject is a mammal, for example a primate such as a human.

Methods of treatment described herein can additionally comprise administering a further compound to reduce, treat or prevent the effect of the bleeding disorder.

The present disclosure also provides a composition comprising a serum albumin variant, or functional fragment thereof, that binds to a blood coagulation factor for use in treating or preventing a bleeding disorder.

The present disclosure also provides use of a composition comprising a serum albumin variant, or functional fragment thereof, that binds to a blood coagulation factor in the manufacture of a medicament for treating or preventing a bleeding disorder.

The present disclosure also provides a kit comprising at least one serum albumin conjugate or composition comprising a serum albumin variant, or functional fragment thereof of the disclosure that binds to a blood coagulation factor packaged with instructions for use in treating or preventing a bleeding disorder in a subject. Optionally, the kit additionally comprises a therapeutically active compound or drug.

The present disclosure also provides a kit comprising at least one serum albumin conjugate or composition comprising a serum albumin variant, or functional fragment thereof of the disclosure that binds to a blood coagulation factor packaged with instructions to administer the conjugate or composition to a subject who is suffering from or at risk of suffering from a bleeding disorder, optionally, in combination with a therapeutically active compound or drug.

Exemplary effects of serum albumin conjugates or compositions of the present disclosure that bind to a blood coagulation factor are described herein and are to be taken to apply mutatis mutandis to the examples of the disclosure set out in the previous five paragraphs.

BRIEF DESCRIPTION OF DRAWINGS

FIG. 1 is a graphical representation showing the serum HSA concentration of HSA variants injected into mice expressing human FcRn receptor. (μg/mL; mean±SEM).

KEY TO SEQUENCE LISTING

SEQ ID NO: 1 amino acid sequence of human serum albumin
SEQ ID NO: 2 amino acid sequence of human coagulation Factor VIII
SEQ ID NO: 3 amino acid sequence of human coagulation Factor IX
SEQ ID NO: 4 amino acid sequence of human coagulation Factor X
SEQ ID NO: 5 amino acid sequence of human coagulation Factor VII
SEQ ID NO: 6 amino acid sequence of human von Willebrand factor

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise. Stated another way, any specific example of the present disclosure may be combined with any other specific example of the disclosure (except where mutually exclusive).

Any example of the present disclosure disclosing a specific feature or group of features or method or method steps will be taken to provide explicit support for disclaiming the specific feature or group of features or method or method steps.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

Serum albumin, or blood albumin, is the most abundant blood protein and functions as a carrier protein for steroids, fatty acids and thyroid hormones in the blood, as well as playing a major role in stabilising extracellular fluid volume. For the purposes of nomenclature only and not limitation an exemplary sequence of a human serum albumin is set out in NCBI GenBank Accession ID: AEE60908 and SEQ ID NO: 1. It should be understood that reference to "serum albumin" or "albumin" includes preproalbumin, which comprises the N-terminal peptide, proalbumin and the secreted albumin. Positions of amino acids are referred to herein by reference to the secreted albumin protein consisting of 585 amino acids (e.g., as set out in SEQ ID NO: 1). Albumin comprises three homologous domains, wherein each domain is a product of two subdomains that possess common structural motifs. Domains I, II and III may be defined with reference to human serum albumin (as set forth in SEQ ID NO: 1). For example, domain I comprises amino acids 1 (±1 to 15 amino acids) to 194 (±1 to 15 amino acids) of SEQ ID NO: 1, domain II comprises amino acids 192 (±1 to 15 amino acids) to 387 (±1 to 15 amino acids) of SEQ ID NO: 1 and domain III comprises amino acid residues 381 (±1 to 15 amino acids) to 585 (±1 to 15 amino acids) of SEQ ID NO: 1. The phrase "±1 to 15 amino acids" means that the amino acid residue may deviate by 1 or 2 or 3 or 4 or 5 or 6 or 7 or 8 or 9 or 10 or 11 or 12 or 13 or 14 or 15 amino acids to the C-terminus and/or the N-terminus of the stated amino acid position. Exemplary domains I, II and III are described by Dockal et al (The Journal of Biological Chemistry, 1999, Vol. 274(41): 29303-29310) and Kjeldsen et al (Protein Expression and Purification, 1998, Vol 13: 163-169).

Additional sequences of serum albumin from other species (e.g., primate serum albumin, (such as chimpanzee serum albumin, gorilla serum albumin), rodent serum albumin (such as hamster serum albumin, guinea pig serum albumin, mouse albumin and rat serum albumin), bovine serum albumin, equine serum albumin, donkey serum albumin, rabbit serum albumin, goat serum albumin, sheep serum albumin, dog serum albumin, chicken serum albumin and pig serum albumin) can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)).

As used herein the phrase "corresponding to" in reference to the position of an amino acid in SEQ ID NO: 1 should be understood as reference to an amino acid residue or position within an albumin sequence, and not necessarily a sequence comprising SEQ ID NO: 1. For example, reference to "a position corresponding to amino acid 522 of SEQ ID NO: 1" in an albumin sequence comprising a 10 amino acid N-terminal truncation would necessarily refer to an amino acid at position 512. In one example, the serum albumin comprises a sequence set forth in SEQ ID NO: 1.

Reference to a "functional fragment" of serum albumin should be understood as a reference to a fragment of serum albumin which have retained and exhibit serum albumin functionality (i.e., ability to bind to FcRn). A fragment may comprise or consist of one more domains of albumin, fragments of such domains or combinations thereof.

As used herein "amino acid substitution(s)" refers to the replacement of an amino acid at a particular position in a polypeptide sequence with another amino acid.

As used herein, the term "FcRn" refers to the neonatal Fc receptor, also known as the Brambell receptor, and is a heterodimer of truncated heavy chain of the major histocompatibility complex class 1-like Fc receptor (FCGRT) and beta-2-microglobulin.

As used herein, the terms "variant" or "mutant" or "mutated" refers to a serum albumin which has undergone substitution of one or more amino acids using well known techniques for site directed mutagenesis or any other conventional method.

As used herein, the term "binds" in reference to the interaction of a serum albumin with FcRn means that the interaction is dependent upon the presence of a particular structure (e.g., an antigenic determinant or epitope) on a cell or protein.

As used herein, phrases referring to "increasing affinity" or "increased binding" or "binding being at a higher level" in relation to the interaction of a serum albumin variant with FcRn will be understood to mean that a serum albumin variant, or functional fragment thereof, binds to or associates with FcRn more frequently, more rapidly, with greater duration and/or greater affinity than a human serum albumin as set forth in SEQ ID NO: 1 (e.g., 1.5 fold or 2 fold or 5 fold or 10 fold or 20 fold or 40 fold or 60 fold or 80 fold to 100 fold or 150 fold or 200 fold).

For the purposes of clarification and as will be apparent to the skilled artisan based on the exemplified subject matter herein, reference to "affinity" in this specification is a reference to the interaction, binding or association of a serum albumin variant with FcRn.

For the purposes of clarification and as will be apparent to the skilled artisan based on the description herein, reference to an "affinity of at least about" will be understood to mean that the affinity is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

As used herein, the term "serum half-life" or "plasma half-life" in the context of the present disclosure refers to the period of time required for the concentration or amount of serum albumin in the body to be reduced by 50% (i.e., one half) for example due to degradation and/or clearance or sequestration by natural mechanisms. The skilled person would recognise that the serum half-life of serum albumin in a subject is dependent on various physiological conditions (e.g., health status, body size/weight). In a healthy human subject, the serum half-life of serum albumin is 19 days. Methods for determining the serum half-life of serum albumin are known in the art and include, for example, pharmacokinetic analysis. For the purposes of the present disclosure, an "increase" or "enhanced" serum half-life refers to an elevation or increase in time taken for the serum concentration of the serum albumin variant to be reduced by 50%, compared to a serum albumin set forth in SEQ ID NO: 1.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding domain" shall be taken to mean a region of an antibody that is capable of specifically binding to an antigen, i.e., a $V_H$ or a $V_L$ or an Fv comprising both a $V_H$ and a $V_L$. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., a blood coagulation factor) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs).

As used herein, the term "Fv" shall be taken to mean any protein, whether comprised of multiple polypeptides or a single polypeptide, in which a variable region of the light chain ($V_L$) and a variable region of a heavy chain ($V_H$) associate and form a complex having an antigen binding domain, i.e., capable of specifically binding to an antigen. The $V_H$ and the $V_L$ which form the antigen binding domain can be in a single polypeptide chain or in different polypeptide chains. Furthermore, an Fv of the disclosure (as well as any protein of the disclosure) may have multiple antigen binding domains which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

An "antigen binding fragment" of an antibody comprises one or more variable regions of an intact antibody. Examples of antibody fragments include Fab, Fab', $F(ab')_2$ and Fv fragments; diabodies; linear antibodies; single-chain antibody molecules, half antibodies and multispecific antibodies formed from antibody fragments.

As used herein, the term "condition" refers to a disruption of or interference with normal function, and is not to be limited to any specific condition, and will include diseases or disorders.

As used herein, the term "bleeding condition" or "bleeding disorder" refers to a condition in which there is abnormal blood coagulation, e.g., reduced or insufficient blood coagulation capability and/or abnormal bleeding (internal and/or external), e.g., excessive bleeding.

As used herein, "coagulation factor" refers to a factor that is associated with the formation of a blot clot, i.e., blood coagulation. In one example, the coagulation factor has pro-coagulant activity. Coagulation factors are known in the art and include without limitation Factor I, Factor II, Factor III, Factor V, Factor VII, Factor VIII, Factor IX, Factor X, Factor XI, Factor XII and Factor XIII or an activated form of any of the foregoing. This term also includes recombinant forms of coagulation factors and/or modified forms thereof, e.g., as is known in the art and/or described herein.

As used herein, a subject "at risk" of developing a disease or condition or relapse thereof or relapsing may or may not have detectable disease or symptoms of disease, and may or may not have displayed detectable disease or symptoms of disease prior to the treatment according to the present disclosure. "At risk" denotes that a subject has one or more risk factors, which are measurable parameters that correlate with development of the disease or condition, as known in the art and/or described herein.

As used herein, the terms "treating", "treat" or "treatment" include administering a serum albumin variant conjugate described herein to thereby reduce or eliminate at least one symptom of a specified disease or condition or to slow progression of the disease or condition.

As used herein, the term "preventing", "prevent" or "prevention" includes providing prophylaxis with respect to occurrence or recurrence of a bleeding disease or a symptom of a bleeding disease in an individual. An individual may be predisposed to or at risk of developing the disease or disease relapse but has not yet been diagnosed with the disease or the relapse.

An "effective amount" refers to at least an amount effective, at dosages and for periods of time necessary, to achieve the desired result. For example, the desired result may be a therapeutic or prophylactic result. An effective amount can be provided in one or more administrations. In some examples of the present disclosure, the term "effective amount" is meant an amount necessary to effect treatment of a disease or condition as hereinbefore described. In some examples of the present disclosure, the term "effective amount" is meant an amount necessary to effect a change in a factor associated with a disease or condition as hereinbefore described. For example, the effective amount may be sufficient to effect a change in the level of coagulation. The effective amount may vary according to the disease or condition to be treated or factor to be altered and also according to the weight, age, racial background, sex, health and/or physical condition and other factors relevant to the mammal being treated. Typically, the effective amount will fall within a relatively broad range (e.g., a "dosage" range) that can be determined through routine trial and experimentation by a medical practitioner. Accordingly, this term is not to be construed to limit the disclosure to a specific quantity. The effective amount can be administered in a single dose or in a dose repeated once or several times over a treatment period.

A "therapeutically effective amount" is at least the minimum concentration required to effect a measurable improvement of a particular disease or condition. A therapeutically effective amount herein may vary according to factors such as the disease state, age, sex, and weight of the patient, and the ability of the albumin conjugate to elicit a desired response in the individual. A therapeutically effective amount is also one in which any toxic or detrimental effects of the albumin conjugate are outweighed by the therapeutically beneficial effects. In one example, a therapeutically effective amount shall be taken to mean a sufficient quantity of albumin conjugate to reduce or inhibit one or more symptoms of a bleeding disorder or a complication thereof.

As used herein, the term "prophylactically effective amount" shall be taken to mean a sufficient quantity of the albumin conjugate to prevent or inhibit or delay the onset of one or more detectable symptoms of a bleeding disorder or a complication thereof.

As used herein, the term "subject" shall be taken to mean any animal including humans, for example a mammal. Exemplary subjects include but are not limited to humans and non-human primates. For example, the subject is a human.

Serum Albumin Variants

The present disclosure provides serum albumin variants, or functional fragments thereof, with defined amino acid substitutions compared to a sequence set forth in SEQ ID NO: 1. In one example, a serum albumin variant, or fragment thereof, of the present disclosure comprises a sequence at least about 85% or 90% or 95% or 97% or 98% or 99% identical to a sequence disclosed herein, wherein the serum albumin variant, or fragment thereof, binds to FcRn as described herein according to any example.

The present disclosure provides a serum albumin variant, or functional fragment thereof, comprising one or more amino acid substitutions selected from the group consisting of:
  (i) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1;
  (ii) valine substituted for alanine at a position corresponding to amino acid 552 of SEQ ID NO: 1;
  (iii) an amino acid selected from the group consisting of alanine, glutamic acid, histidine, serine, lysine and arginine substituted for glycine at a position corresponding to amino acid 572 of SEQ ID NO: 1; and
  (iv) combinations thereof.

In one example, the serum albumin variant, or functional fragment thereof further comprises tyrosine substituted for lysine at a position corresponding to amino acid 573 of SEQ ID NO: 1.

For example, the inventors have identified several amino acid residues in a sequence set forth in SEQ ID NO: 1 that can be substituted without loss of function or that result in improved function. In one example, the serum albumin variant, or functional fragment thereof, comprises between 1 and 3 amino acid substitutions at a position corresponding to amino acid 522, 552 and/or 572 compared to a sequence set forth in SEQ ID NO: 1. For example, the serum albumin variant, or functional fragment thereof, comprises 1 or 2 or 3 amino acid substitutions at a position corresponding to amino acid 522, 552 and/or 572 compared to a sequence set forth in SEQ ID NO: 1

Optionally, the serum albumin variant, or functional fragment thereof additionally comprises 1 amino acid substitution at a position corresponding to amino acid 573 compared to a sequence set forth in SEQ ID NO: 1. In one example, the serum albumin variant, or functional fragment thereof, comprises between 1 and 4 amino acid substitutions at a position corresponding to amino acid 522, 552 and/or 572 and optionally 573 compared to a sequence set forth in SEQ ID NO: 1. For example, the serum albumin variant or functional fragment thereof, comprises 1 or 2 or 3 or 4 amino acid substitutions at a position corresponding to amino acid 522, 552 and/or 572 and optionally 573 compared to a sequence set forth in SEQ ID NO: 1.

In one example, a serum albumin variant, or functional fragment thereof, of the present disclosure comprises a variant of a sequence set forth in SEQ ID NO: 1, wherein the variant sequence at least comprises a glycine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a isoleucine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a lysine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a methionine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a phenylalanine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a tryptophan at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a tyrosine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a valine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises an alanine at a position corresponding to amino acid 522 of SEQ ID NO: 1.

In one example, a serum albumin variant, or functional fragment thereof, of the present disclosure comprises a variant of a sequence set forth in SEQ ID NO: 1, wherein the variant sequence at least comprises a valine at a position corresponding to amino acid 552 of SEQ ID NO: 1.

In one example, a serum albumin variant, or functional fragment thereof, of the present disclosure comprises a variant of a sequence set forth in SEQ ID NO: 1, wherein the variant sequence at least comprises an alanine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a glutamic acid at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a histidine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a serine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a lysine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises an arginine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a valine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1 and an arginine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1 and a valine at a position corresponding to amino acid 552 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1 and a tyrosine at a position corresponding to amino acid 573 of SEQ ID NO: 1.

In one example, a serum albumin variant, or functional fragment thereof, of the present disclosure comprises a variant of a sequence set forth in SEQ ID NO: 1, wherein the variant sequence at least comprises a valine at a position corresponding to amino acid 552 of SEQ ID NO: 1 and a tyrosine at a position corresponding to amino acid 573 of SEQ ID NO: 1.

In one example, a serum albumin variant, or functional fragment thereof, of the present disclosure comprises a variant of a sequence set forth in SEQ ID NO: 1, wherein the variant sequence at least comprises an arginine at a position corresponding to amino acid 572 of SEQ ID NO: 1 and a tyrosine at a position corresponding to amino acid 573 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1, a valine at a position corresponding to amino acid 552 of SEQ ID NO: 1, and an arginine at a position corresponding to amino acid 572 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1, a valine at a position corresponding to amino acid 552 of SEQ ID NO: 1, and a tyrosine at a position corresponding to amino acid 573 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1, an arginine at a position corresponding to amino acid 572 of SEQ ID NO: 1, and a tyrosine at a position corresponding to amino acid 573 of SEQ ID NO: 1.

In one example, a serum albumin variant, or functional fragment thereof, of the present disclosure comprises a variant of a sequence set forth in SEQ ID NO: 1, wherein the variant sequence at least comprises a leucine at a position corresponding to amino acid 522 of SEQ ID NO: 1, a valine at a position corresponding to amino acid 552 of SEQ ID NO: 1, an arginine at a position corresponding to amino acid 572 of SEQ ID NO: 1, and a tyrosine at a position corresponding to amino acid 573 of SEQ ID NO: 1.

Exemplary methods for producing variant forms of serum albumin are described herein or known in the art and include:
  mutagenesis of DNA (Thie et al., *Methods Mol. Biol.* 525: 309-322, 2009) or RNA (Kopsidas et al., *Immunol. Lett.* 107:163-168, 2006; Kopsidas et al. *BMC Biotechnology,* 7: 18, 2007; and WO1999/058661);
  introducing a nucleic acid encoding the polypeptide into a mutator cell, e.g., XL-1Red, XL-mutS and XL-mutS-Kanr bacterial cells (Stratagene);
  DNA shuffling, e.g., as disclosed in Stemmer, *Nature* 370: 389-91, 1994; and site directed mutagenesis, e.g., as described in Dieffenbach (ed) and Dveksler (ed) (In: PCR Primer: A Laboratory Manual, Cold Spring Harbor Laboratories, N Y, 1995).

Exemplary methods for determining biological activity of the serum albumin variant, or functional fragment thereof, of the disclosure will be apparent to the skilled person and/or described herein, e.g., FcRn affinity. For example, methods for determining affinity of the serum albumin variant, or functional fragment thereof, include affinity, association, dissociation and therapeutic efficacy are described herein.

For example, the inventors have identified several amino acid residues in a sequence set forth in SEQ ID NO: 1 that can be substituted to increase the half-life of the serum albumin. For example, the serum albumin variant, or functional fragment thereof comprises one or more amino acid substitutions that increase the affinity of the albumin for the neonatal Fc receptor (FcRn). In one example, the variant or functional fragment thereof binds with increased affinity to FcRn compared to a serum albumin set forth in SEQ ID NO: 1. For example, the serum albumin variant, or functional fragment thereof, has increased affinity for FcRn at lower pH, e.g., about pH 6.0, to facilitate albumin/FcRn binding in an endosome. In one example, the albumin has increased affinity for FcRn at about pH 6 compared to its affinity at about pH 7.4, which facilitates the re-release of albumin into blood following cellular recycling. These amino acid substitutions are useful for extending the half-life of a protein, by reducing clearance from the blood.

In one example, exemplary amino acid substitutions include Q522G, Q522I, Q522K, Q522M, Q522L, Q522F, Q522W, Q522Y, Q522V, A552V, G572A, G572E, G572H, G572S, G572K and G572R.

In another example, exemplary amino acid substitutions include Q522G, Q522I, Q522K, Q522M, Q522L, Q522F, Q522W, Q522Y, Q522V, Q522A, A552V, G572A, G572E, G572H, G572S, G572K, G572V and G572R Conjugates In one example, a serum albumin variant or functional fragment thereof, of the present disclosure is conjugated to a compound and/or encapsulates another compound. For example, the compound is selected from the group consisting of a radioisotope, a detectable label, a therapeutic compound, a therapeutic protein, an imaging agent, a colloid, a toxin, a nucleic acid, a peptide, a protein, a small molecule, antisense oligonucleotide, a short hairpin RNA (shRNA), a siRNA, an interfering RNA (RNAi), a ribozyme, a microRNA, a microRNA adapted shRNA (shRNAmir), a DNAzyme and mixtures thereof.

The compound can be directly or indirectly bound to the serum albumin variant or functional fragment thereof (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal or quantum dot), a therapeutic compound or protein (e.g., a chemotherapeutic or an anti-inflammatory or coagulation factor), a colloid (e.g., gold), a toxin (e.g., ricin or tetanus toxoid), a nucleic acid, a protein (e.g., a protein comprising an antigen binding domain of an antibody), and mixtures thereof. In one example, the serum albumin variant or functional fragment thereof, is conjugated to a coagulation factor.

For example, the compound is a protein and is conjugated to the serum albumin variant or functional fragment thereof by an amine bond.

In one example, disclosure provides a fusion protein comprising the serum albumin variant or functional fragment thereof and the compound (e.g., a therapeutic protein, such as a coagulation factor). For example, the compound is positioned at N-terminus of the serum albumin variant or functional fragment thereof, C-terminus of the serum albumin variant or functional fragment thereof, inserted into a loop in the serum albumin variant or functional fragment thereof or any combination thereof.

Exemplary compounds that can be conjugated to a serum albumin variant of the disclosure and methods for such conjugation are known in the art and described herein.

Radioisotopes

In one example, the present disclosure provides a serum albumin variant, or functional fragment thereof, conjugated to a radioisotope.

Radioisotopes suitable for use in the present disclosure will be apparent to the skilled person and include, for example, iodine-123 ($^{123}$I), iodine-125 ($^{125}$I), iodine-130 ($^{130}$I), iodine-133 ($^{133}$I), iodine-135 ($^{135}$I), scandium-47 ($^{47}$Sc), arsenic-72 ($^{72}$As), scandium-72 ($^{72}$Sc), yttrium-90 ($^{90}$Y), yttrium-88 ($^{88}$Y), ruthenium-97 ($^{97}$Ru), palladium-100 ($^{100}$Pd) rhodium-101m ($^{101m}$Rh), antimony 119 ($^{119}$Sb), barium 128 ($^{128}$Ba), mercury-197 ($^{197}$Hg), astatine-211 ($^{211}$At), bismuth-212 ($^{212}$Bi) samarium 153 ($^{153}$Sm), europium 169 ($^{169}$Eu), lead 212 (212Pb), palladium-109 ($^{199}$Pd), indium-111 ($^{111}$In), $^{67}$Gu, $^{68}$Gu, Copper-67 ($^{67}$Cu), bromine-75 ($^{75}$Br), bromine-76 ($^{76}$Br), bromine-77 ($^{77}$Br), technetium-99m ($^{99m}$Tc), carbon-11 ($^{11}$C), nitrogen-13 ($^{13}$N), oxygen-15 ($^{15}$O), iodine-18 ($^{18}$4 rhenium-188 ($^{188}$Re), lead-203 ($^{203}$Pb), copper-64 ($^{64}$Cu), rhodium-105 ($^{105}$Rh), gold-198 ($^{198}$Au), argon-199 ($^{199}$Ag) or lutetium-177 ($^{177}$Lu).

Detectable Labels

In one example, the present disclosure provides a serum albumin variant, or functional fragment thereof, conjugated to a detectable label. For example, the detectable label is a fluorophore, a fluorescent nanocrystal or quantum dot.

The term "fluorophore" refers to a chemical compound that absorbs light at a specific wavelength and fluoresces, or re-emits light, at a longer wavelength. Fluorophores may fluoresce in the ultraviolet spectrum (10 nm to 400 nm), visible spectrum (400 nm to 700 nm), or near infrared region (680 nm to 100,000 nm).

Suitable fluorophores for use in the present disclosure will be apparent to the skilled and include, for example, indocyanine green, IRDye78, IRDye80, IRDye38, IRDye40, IRDye41, IRDye700, IRDye800, IRDye800CW, Cy5, Cy5.5, Cy7, DRAQSNO, Licor NIR, Alexa Fluor488, Alexa Fluor680, Alexa Fluor 700, Alexa Fluor750, La Jolla Blue, R-phycoerythrin (PE), hydroxycoumarin, methoxycoumarin, aminocoumarin, Fluorescein FITC, Rhodamine Red-X, Texas Red, Allophycocyanin (APC) and analogs thereof.

In one example, the detectable label is a quantum dot. Quantum dots are a semiconductor nanocrystal with size-dependent optical and electronic properties. Exemplary materials suitable for use as quantum dots include ZnS, ZnSe, ZnTe, CdS, CdSe, CdTe, GaN, GaP, GaAs, GaSb, InP, InAs, Sb, AlS, AlP, AlAs, AlSb, PbS, PbSe, Ge, and Si and ternary and quaternary mixtures thereof.

In one example, the detectable label is a fluorescent protein. Suitable fluorescent proteins for use in the present disclosure will be apparent to the skilled person and include, for example, Renilla luciferase, green fluorescent protein (GFP), cyan fluorescent protein (CFP), red fluorescent protein (RFP), blue fluorescent protein (BFP), yellow fluorescent protein (YFB) and derivatives thereof.

Biological Entities
Coagulation Factors

The present disclosure provides a serum albumin variant, or functional fragment thereof, conjugated to a coagulation factor.

Blood coagulation occurs through a cascade of stages involving release of several coagulation factors, ultimately resulting in the formation of a blood clot containing insoluble fibrin. Exemplary coagulation factors include, but are not limited to, Factor I (Fibrinogen), Factor II (Prothrombin/thrombin), Factor III (Tissue factor), Factor V (Labile factor), Factor VII (Proconvertin), Factor VIII (Antihaemophilic factor), Factor IX (Christmas factor), Factor X (Stuart-Prower factor), Factor XI (Plasma thromboplastin antecedent), Factor XII (Hageman (contact) factor) and Factor XIII (Fibrin-stabilizing factor/Prekallikrein (Fletcher) factor/HMWK (Fitzgerald) factor).

For example, the compound is a coagulation factor and is conjugated to the serum albumin variant or functional fragment thereof by an amine bond.

In one example, disclosure provides a fusion protein comprising the serum albumin variant or functional fragment thereof and a coagulation factor. For example, the coagulation factor is positioned at N-terminus of the serum albumin variant or functional fragment thereof, C-terminus of the serum albumin variant or functional fragment thereof, inserted into a loop in the serum albumin variant or functional fragment thereof or any combination thereof.

In one example, the coagulation factor is Factor VIII. For the purposes of nomenclature only and not limitation, exemplary sequences of human Factor VIII are set out in NCBI Ref Seq ID NP_000123, protein accession number NM_000132.3 and in SEQ ID NO: 2.

In one example, the coagulation factor is Factor IX. For the purposes of nomenclature only and not limitation, exemplary sequences of human Factor IX are set out in GenBank ID AAA98726.1 and in SEQ ID NO: 3.

In one example, the coagulation factor is Factor X. For the purposes of nomenclature only and not limitation, exemplary sequences of human Factor X are set out in Gene ID: 2159 and in SEQ ID NO: 4.

In one example, the coagulation factor is Factor VII. For the purposes of nomenclature only and not limitation, exemplary sequences of human Factor VII are set out in Ref Seq ID NM_00131 and in SEQ ID NO: 5.

For the purposes of nomenclature only and not limitation, exemplary sequences of human Factor I are set out in NCBI Ref Seq ID NM_000508 (alpha chain) and NM_005141 (beta chain), exemplary sequences of human Factor II are set out in Ref Seq ID NM_000506, exemplary sequences of human Factor III are set out in Ref Seq ID NM_001993, exemplary sequences of human Factor V are set out in Ref Seq ID NM_000130, exemplary sequences of human Factor XI are set out in Ref Seq ID NM_000128, exemplary sequences of human Factor XII are set out in Ref Seq ID NM_000505, exemplary sequences of human Factor XIII are set out in Ref Seq ID NM_000129 (A chain) and NM_001994 (B chain).

Additional sequence of coagulation factors can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)).

Exemplary coagulation factors may be plasma derived from a donor or a recombinant protein. For example, the coagulation factor is a plasma derived or recombinant coagulation factor protein. For example, the therapeutic protein is selected from the group consisting of Factor I (Fibrinogen), Factor II ((prothrombin)/thrombin), Factor III (Tissue Factor), Factor V (Labile Factor), Factor VII (Proconvertin), Factor VIIa (e.g., NOVOSEVEN®), Factor VIII (Antihaemophilic Facto; such as a single chain recombinant Factor VIII, e.g., as described in Zollner et al., *Thromb Res.* 132:280-287, 2013; or a plasma derived Factor VIII product, such as FEIBA®, MONOCLATE-P®, or BIOSTATE®; or a recombinant Factor VIII product, such as ADVATE®, ELOCTATE®, RECOMBINATE®, KOGENATE FS®, HELIXATE® Fs, HELIXATE®, XYNTHA®/REFACTO AB®, HEMOFIL-M®, MONARC-M®, ALPHANATE®, KOATE-DVI®, NUWIQ® or HYATE:C®), Factor IX (Christmas Factor, e.g., a plasma derived Factor IX product such as, BERININ® P, MONOFIX® or MONONINE®; or a recombinant Factor IX product such as ALPHANINE SD®, ALPROLIX®, BEBULIN®, BEBULIN VH®, BENEFIX®, IXINITY®, PROFILNINE SD®, PROPLEX T®, or RIXUBIS®), Factor X (Stuart-Prower Factor), Factor XI (Plasma thromboplastin antecedent), Factor XII (Hageman (contact) factor) and Factor XIII ((Fibrin-stabilizing factor/Prekallikrein (Fletcher) factor/HMWK (Fitzgerald) factor; e.g., FIBROGAMMIN® P, CORIFACT®, CLUVOT® or CLUVIAT®). In one example, the therapeutic protein is a von Willebrand Factor/FVIII complex (e.g., HUMATE-P®, HAEMATE®-P, BIOSTATE® or VONCENTO®). In an alternative example, the therapeutic protein is a prothrombin complex (e.g., BERIPLEX® P/N, CONFIDEX® or KCENTRA®). In another example, the therapeutic protein is a fibrinogen (e.g., RIASTAP®, HAEMOCOMPLETTAN® P).

Von Willebrand Factor

The present disclosure provides a serum albumin variant, or functional fragment thereof, conjugated to von Willebrand factor.

The term "von Willebrand factor" (vWF) as used herein includes naturally occurring (native) VWF, but also variants thereof, e.g., fragments, fusion proteins or conjugates, or sequence variants where one or more residues have been inserted, deleted or substituted, retaining the biological activity of naturally occurring vWF. For the purposes of nomenclature only and not limitation, exemplary sequences of human native vWF are set out in NCBI Ref Seq ID: NP_000543.2 and SEQ ID NO: 6. The skilled person will appreciate that the native vWF comprises multiple domains. For the purposes of the present disclosure, the following annotations have been prescribed: D1-D2-D'-D3-A1-A2-A3-D4-C1-C2-C3-C4-C5-C6-CK, wherein the D' domain consists of amino acids 764 to 865 of SEQ ID NO: 6; the D3 domain consists of amino acids 866 to 1242 of SEQ ID NO: 6; and the C1 domain consists of amino acids 2255 to 2328 of SEQ ID NO: 6.

In one example, the vWF is a modified or mutant or variant vWF. For example, the modified vWF for use in the present disclosure comprises a D'D3 domain and modified forms thereof, such as truncated or mutated forms thereof. For example, the modified vWF comprises amino acids 764 to 1242 of SEQ ID NO: 6.

In one example, the von Willebrand factor is a recombinant von Willebrand factor.

Soluble Complement Inhibitors

The present disclosure provides a serum albumin variant, or functional fragment thereof, conjugated to a soluble complement inhibitor.

The complement system is comprised of a number of cell-surface and soluble proteins that play a role in elimination of foreign microorganisms, whilst protecting the host from complement-related damage. The three pathways of the complement system include the classical pathway (involving C1q, C1r, C1s, C4, C2 and C3 components), the lectin pathway and the alternative pathway. Four complement receptors have been described, CR1 (CD35), CR2 (CD21), CR3 (CD11b/CD18) and CR4 (CD11c/CD18). CR1 is a principal regulator of the activation of the complement system of plasma proteins.

In one example, the serum albumin variant, or functional fragment thereof, is conjugated to a soluble complement inhibitor, or modified (i.e., variant) form thereof.

Suitable complement inhibitors for use in the present disclosure will be apparent to the skilled person and include, for example, Factor I, (fI), Factor H (fH), C4b-binding protein (C4 bp), soluble CD55 (decay accelerating factor (DAF)), C1-inhibitor (C1-INH or C1 esterase inhibitor); soluble CD35 (sCR1); soluble CD46 (membrane cofactor protein (MCP)), soluble CD59 (protectin), TT30 (CR2-fH), Cobra venom factor (CVF) and a functional fragment or variant thereof.

In one example, the complement inhibitor is a soluble complement receptor 1 (sCR1), also known as complement receptor type 1; CD35; C3BR; C3b/C4b receptor, and TP10. For example, the soluble complement inhibitor for use in the present disclosure is a modified or variant sCR1. sCR1 and variant sCR1 molecules will be apparent to the skilled person and are described, for example, in WO1991016437, WO1994000571 and WO1997031944.

In one example, the complement inhibitor is a C1-inhibitor (C1-INH), also known as C1 esterase inhibitor, serpin family G member 1 (SERPING1), HAE1, HAE2, C1NH and C1IN. For example, the complement inhibitor for use in the present disclosure is a modified or variant C1-INH. In one example, the C1-INH is plasma-derived C1-INH. In another example, the C1-INH is recombinant C1-INH. C1-INH and variant C1-INH molecules will be apparent to the skilled person and include, for example, Berinert®. Other suitable C1-INH and variant C1-INH molecules are described, for example, in WO2016070156.

Toxins

The present disclosure provides a serum albumin variant, or functional fragment thereof, conjugated to a toxin.

Suitable toxins for use in the present disclosure will be apparent to the skilled person and include, for example, ricin, abrin, diphtheria toxin, tetanus toxoid, *Pseudomonas* exotoxin A (PE), and ribosomal inactivating proteins such as gelonin, pokeweed antiviral protein and saporin.

Chemotherapy Compounds

The present disclosure provides a serum albumin variant, or functional fragment thereof, conjugated to a chemotherapy compound.

Suitable chemotherapy compounds for use in the present disclosure will be apparent to the skilled person and include, for example, caboplatin, cisplatin, cyclophosphamide, docetaxal, doxorubicin, erlotinib, etoposide, fluorouracil, irinotecan, methotrexate, paclitaxel, topotecan, vincristine, vinblastine, methotrexate, l-asparaginase, vincristine, doxorubicin, danorubicin, cytarabine, idarubicin, mitoxantrone, cyclophosphamide, fludarabine, chlorambucil and derivatives thereof.

Antibodies or Antigen Binding Fragments

In one example, the present disclosure provides a serum albumin variant, or functional fragment thereof, conjugated to an antibody or antigen binding fragment thereof.

Exemplary antibodies or antigen binding fragments thereof for use in the present disclosure are described herein or known in the art and include:

a humanized antibody or fragment thereof, e.g., a protein comprising a human-like variable region, which includes CDRs from an antibody from a non-human species (e.g., mouse or rat or non-human primate) grafted onto or inserted into FRs from a human antibody (e.g., produced by methods described in U.S. Pat. Nos. 5,225,539, 6,054,297, 7,566,771 or U.S. Pat. No. 5,585,089)

a human antibody or fragment thereof, e.g., antibodies having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (e.g., produced by methods described in U.S. Pat. No. 5,565,332) and affinity matured forms of such antibodies.

a synhumanized antibody or fragment thereof, e.g., an antibody that includes a variable region comprising FRs from a New World primate antibody variable region and CDRs from a non-New World primate antibody variable region (e.g., produced by methods described in WO2007019620).

a primatized antibody or fragment thereof, e.g., an antibody comprising variable region(s) from an antibody generated following immunization of a non-human primate (e.g., a cynomolgus macaque) (e.g., produced by methods described in U.S. Pat. No. 6,113,898).

a chimeric antibody or chimeric antigen binding fragment, e.g., an antibody or fragment in which one or more of the variable domains is from a particular species (e.g., murine, such as mouse or rat) or belonging to a particular antibody class or subclass, while the remainder of the antibody or fragment is from another species (such as, for example, human or non-human primate) or belonging to another antibody class or subclass (e.g., produced by methods described in U.S. Pat. Nos. 6,331,415; 5,807,715; 4,816,567 and 4,816,397).

a deimmunized antibody or antigen binding fragment thereof, e.g., antibodies and fragments that have one or more epitopes, e.g., B cell epitopes or T cell epitopes removed (i.e., mutated) to thereby reduce the likelihood that a subject will raise an immune response against the antibody or protein (e.g., as described in WO2000034317 and WO2004108158).

a bispecific antibody or fragment thereof, e.g., an antibody comprising two types of antibodies or antibody fragments (e.g., two half antibodies) having specificities for different antigens or epitopes (e.g., as described in U.S. Pat. No. 5,731,168).

Additional exemplary antibody fragments for use in the present disclosure are described herein or known in the art and include:

single-domain antibodies (domain antibody or dAb), e.g., a single polypeptide chain comprising all or a portion of the heavy chain variable domain of an antibody.

a diabody, triabody, tetrabody or higher order protein complex (e.g., as described in WO98/044001 and/or WO94/007921).

single chain Fv (scFv) fragments, e.g., a fragment comprising $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv).

a half-antibody or a half-molecule, e.g., a protein comprising a single heavy chain and a single light chain.

The present disclosure also contemplates other antibodies and antibody fragments, such as:

(i) minibodies, e.g., as described in U.S. Pat. No. 5,837,821;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

Protein Scaffolds

In one example, the present disclosure provides a serum albumin variant, or functional fragment thereof, conjugated to a protein scaffold. For example, the protein scaffold is an immunoglobulin or immunoglobulin fragment.

Suitable protein scaffolds for use in the present disclosure are described herein or will be apparent to the skilled person and include:

heavy chain immunoglobulins, e.g., immunoglobulins (e.g., antibodies) that do not comprise a light chain (e.g., as described in WO9404678, WO9749805 and WO 9749805).

V-like proteins, e.g., a T-cell receptor comprising two V-domains that combine into a structure similar to the Fv module of an antibody (e.g., as described in Novotny et al., Proc Natl Acad Sci USA 88: 8646-8650, 1991, WO1999045110 or WO2011107595).

adnectins e.g., an immunoglobulin based on the tenth fibronectin type III (10Fn3) domain of human fibronectin in which the loop regions are altered to confer antigen binding (e.g., as described in US20080139791 or WO2005056764).

anticalins e.g., an immunoglobulin derived from lipocalins having a rigid β-sheet secondary structure with a plurality of loops at the open end of the conical structure which can be engineered to bind to an antigen (e.g., as described in U.S. Pat. No. 7,250,297 or US20070224633).

an affibody e.g., a scaffold derived from the Z domain (antigen binding domain) of Protein A of *Staphylococcus aureus* which can be engineered to bind to antigen (e.g., as described in EP1641818).

an avimer, e.g., multidomain proteins derived from the A-domain scaffold family (e.g., as described in WO2002088171).

Designed Ankyrin Repeat Protein (DARPin), e.g., derived from the Ankyrin family of proteins that mediate attachment of integral membrane proteins to the cytoskeleton that can be engineered to bind different target antigens (e.g., as described in US20040132028).

Small Molecules

In one example, the present disclosure provides a serum albumin variant, or functional fragment thereof, conjugated to a small molecule. Such a small molecule may be isolated from a library. Chemical small molecule libraries are available commercially or alternatively may be generated using methods known in the art, such as, for example, those described in U.S. Pat. No. 5,463,564.

Techniques for synthesizing small organic compounds will vary considerably depending upon the compound, however such methods will be known to those skilled in the art.

In one example, informatics is used to select suitable chemical building blocks from known compounds, for producing a combinatorial library. For example, QSAR (Quantitative Structure Activity Relationship) modeling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and log P (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens can be used to expand the list of compounds being screened to thereby identify highly active compounds.

Nucleic Acid-Based Agents

In one example, the present disclosure provides a serum albumin variant, or functional fragment thereof, conjugated to a nucleic acid-based agent. Suitable agents will be apparent to the skilled person and include, for example, an antisense oligonucleotide, a short hairpin RNA (shRNA), siRNA, an interfering RNA (RNAi), a ribozyme, a microRNA and a DNAzyme.

Antisense Oligonucleotides

In one example, the nucleic acid-based agent is an antisense oligonucleotide or antisense nucleic acid.

The terms "antisense oligonucleotide" or "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid. The full-length sequence complementary to the entire gene transcript may be used. The length can be 100-2000 nucleotides. The degree of identity of the antisense sequence to the targeted transcript should be at least 90%, for example, 95-100%.

Catalytic Nucleic Acid

In one example, the nucleic acid-based agent is a catalytic nucleic acid.

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

In one example, the nucleic acid-based agent is a small interfering RNA ("siRNA") molecule.

RNA interference (RNAi) is useful for specifically inhibiting production of a particular protein. Without being limited by theory, this technology relies on the presence of dsRNA molecules that contain a sequence that is essentially identical to the mRNA of the gene of interest or part thereof. Conveniently, dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the subject in which it is to be introduced, for example as determined by standard BLAST search.

Assaying Activity of a Serum Albumin Variant

Serum albumin variants of the present disclosure are readily screened for biological activity, e.g., as described below.

Determining Affinity

Optionally, the dissociation constant (Kd) or association constant (Ka) or affinity constant ($K_D$) of a serum albumin variant, or functional fragment thereof, is determined.

Affinity measurements can be determined by standard methodology, for example, immunoassays, surface plasmon resonance (SPR; e.g., using BIAcore surface plasmon resonance (BIAcore, Inc., Piscataway, N.J.) (Rich and Myszka *Curr. Opin. Biotechnol* 11: 54, 2000; Englebienne *Analyst.* 123: 1599, 1998), isothermal titration calorimetry (ITC) or other kinetic interaction assays known in the art.

In some examples, the serum albumin variant, or functional fragment thereof has a similar $K_D$ or an improved $K_D$ (i.e., a $K_D$ value lower than) than a serum albumin set forth in SEQ ID NO: 1.

Binding affinity for FcRn can also be determined non-quantitatively using flow cytometry. For example, CHO cells stably expressing the serum albumin variant, or functional fragment thereof, are stained with alexa-488 labeled FcRn/β2m (to detect target binding) and anti-myc-alexa 647 (to detect expression) at acidic (pH 5.5) and neutral (pH 7.4) pH and analysed by flow cytometry. Relative binding to FcRn/β2m is determined, for example, by calculating mean fluorescence intensity relative to an unmodified serum albumin (e.g., as set forth in SEQ ID NO: 1).

Determining Half-Life

Serum albumin variants, or functional fragments thereof, encompassed by the present disclosure have an improved half-life, e.g., are modified to extend their half-life compared to a serum albumin set forth in SEQ ID NO: 1 (i.e., a serum albumin that is unmodified). Methods for determining a serum albumin variant, or functional fragment thereof, with an increased half-life will be apparent to the skilled person. For example, the ability of a serum albumin variant, or functional fragment thereof, to bind to a neonatal Fc receptor (FcRn) is assessed. In this regard, increased binding affinity for FcRn increases the serum half-life of the serum albumin variant, or functional fragment thereof (see for example, Kim et al., *Eur J Immunol.*, 24:2429, 1994).

The half-life of a serum albumin variant, or functional fragment thereof, of the disclosure can also be measured by pharmacokinetic studies, e.g., according to the method described by Kim et al, *Eur J of Immunol* 24:542, 1994. According to this method protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein (i.e., as set forth in SEQ ID NO: 1).

In vitro Cellular Assays

Various in vitro assays are available to assess the ability of a serum albumin variant, or functional fragment thereof, to treat a disease or condition described herein.

In one example, the uptake and recycling of the serum albumin variant, or functional fragment thereof, is tested in an in vitro cellular assay.

Methods of assessing cellular uptake and recycling are known in the art and/or exemplified herein. For example, fluorescently labelled serum albumin variant is incubated with cells expressing the human FcRn receptor on the cell surface. After addition of the labelled serum albumin variant the progress of the protein recycling can be tracked and compared to a non-modified serum albumin protein by methods including flow cytometry and fluorescence microscopy (for example, confocal fluorescence microscopy). Changes to the normal recycling pathway for a particular serum albumin variant can be identified and characterised.

Serum albumin variants, or functional fragments thereof, that are found to be effectively recycled are identified as variants of the present disclosure.

Pharmacokinetic Analysis

In one example, the pharmacokinetic (PK) properties of the serum albumin variant, or functional fragment thereof, will be assessed.

Methods of assessing the PK properties are known in the art and/or are exemplified herein. For example, serum albumin variants are injected into transgenic mice expressing human FcRn receptor or other suitable mammalian hosts (e.g. rats, cynomolgus monkeys). In one example, the transgenic mice expressing human FcRn receptor are "hFcRn Tg32" homozygous mice (i.e., B6. Cg-FcgrttmlDcr Tg(FCGRT)32Dcr/DcrJ; The Jackson Laboratory stock number 014565; or as described in Roopenian et al., J. Immunol 2003; 170:3528-3533). Plasma levels of serum albumin will be assessed using ELISA using commercially available methods.

Pharmaceutical Compositions

Suitably, in compositions or methods for administration of the serum albumin variant, or functional fragment thereof, of the disclosure to a subject, the serum albumin conjugate of the present disclosure (i.e., the serum albumin variant, or functional fragment thereof conjugated to a compound) is combined with a pharmaceutically acceptable carrier as is understood in the art. Accordingly, one example of the present disclosure provides a composition (e.g., a pharmaceutical composition) comprising the serum albumin conjugate of the disclosure combined with a pharmaceutically acceptable carrier.

In general terms, by "carrier" is meant a solid or liquid filler, binder, diluent, encapsulating substance, emulsifier, wetting agent, solvent, suspending agent, coating or lubricant that may be safely administered to any subject, e.g., a human. Depending upon the particular route of administration, a variety of acceptable carriers, known in the art may be used, as for example described in Remington's Pharmaceutical Sciences (Mack Publishing Co. N.J. USA, 1991).

A serum albumin conjugate of the present disclosure is useful for parenteral, topical, oral, or local administration, aerosol administration, or transdermal administration, for prophylactic or for therapeutic treatment. In one example, the serum albumin conjugate is administered parenterally, such as subcutaneously or intravenously. For example, the serum albumin conjugate is administered intravenously.

Formulation of a serum albumin conjugate to be administered will vary according to the route of administration and formulation (e.g., solution, emulsion, capsule) selected. An appropriate pharmaceutical composition comprising a serum albumin conjugate to be administered can be prepared in a physiologically acceptable carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The serum albumin conjugate can be stored in the liquid stage or can be lyophilized for storage and reconstituted in a suitable carrier prior to use according to art-known lyophilization and reconstitution techniques.

Conditions to be Treated

As discussed herein, the present disclosure provides a method of treating or preventing a disease or condition in a subject, the method comprising administering the serum albumin conjugate of the present disclosure or the composition of the present disclosure to a subject in need thereof. In one example, the present disclosure provides a method of treating a disease or condition in a subject in need thereof.

The present disclosure also provides for use of a serum albumin conjugate of the present disclosure for treating or preventing a disease or condition in a subject comprising administering the serum albumin conjugate of the present disclosure or the composition of the present disclosure to a subject in need thereof. In one example, the present disclosure provides for use of a serum albumin conjugate of the present disclosure for treating a disease or condition in a subject in need thereof.

In one example, the disease or condition is a bleeding disorder.

In one example, the subject suffers from a bleeding disorder. The bleeding disorder can be inherited or acquired. For example, a subject suffering from a bleeding disorder has suffered a symptom of a bleeding disorder, such as:

Easy bruising;
Bleeding gums;
Heavy bleeding from small cuts or dental work;
Unexplained nosebleeds;
Heavy menstrual bleeding;
Bleeding into joints; and/or
Excessive bleeding following surgery.

In one example, the subject is at risk of developing a bleeding disorder. A subject is at risk if he or she has a higher risk of developing a bleeding disorder than a control population. The control population may include one or more subjects selected at random from the general population (e.g., matched by age, gender, race and/or ethnicity) who have not suffered from or have a family history of angina, stroke and/or heart attack. A subject can be considered at risk for a bleeding disorder if a "risk factor" associated with a bleeding disorder is found to be associated with that subject. A risk factor can include any activity, trait, event or property associated with a given disorder, for example, through statistical or epidemiological studies on a population of subjects. A subject can thus be classified as being at risk for a bleeding disorder even if studies identifying the underlying risk factors did not include the subject specifically. For example, a subject who has excessive bleeding is at risk of developing a bleeding disorder because the frequency of a bleeding disorder is increased in a population of subjects who have excessive bleeding as compared to a population of subjects who do not.

In one example, the subject is at risk of developing a bleeding disorder and the serum albumin conjugate is administered before or after the onset of symptoms of a bleeding disorder. In one example, the serum albumin conjugate is administered before the onset of symptoms of a bleeding disorder. In one example, the serum albumin conjugate is administered after the onset of symptoms of a bleeding disorder. In one example, the serum albumin conjugate of the present disclosure is administered at a dose that alleviates or reduces one or more of the symptoms of a bleeding disorder in a subject at risk.

The methods of the present disclosure can be readily applied to any form of bleeding disorder in a subject.

A method of the present disclosure may also include co-administration of the serum albumin conjugate according to the disclosure together with the administration of another therapeutically effective agent for the prevention or treatment of a bleeding disorder.

In one example, the serum albumin conjugate of the disclosure is used in combination with at least one additional known compound or therapeutic protein which is currently being used or is in development for preventing or treating bleeding disorders. Compounds currently used in the treatment of bleeding disorders are known in the art. Exemplary therapeutic proteins may be plasma derived from a donor or a recombinant protein. For example, the therapeutic protein is a plasma derived or recombinant coagulation factor protein. For example, the therapeutic protein is selected from the group consisting of Factor I, Factor II ((prothrombin)/thrombin), Factor III, Factor V, Factor VII, Factor VIIa (e.g., NOVOSEVEN®), Factor VIII (such as a single chain recombinant Factor VIII, e.g., as described in Zollner et al., *Thromb Res.* 132:280-287, 2013; or a plasma derived Factor VIII product, such as FEIBA®, MONOCLATE-P®, or BIOSTATE®; or a recombinant Factor VIII product, such as ADVATE®, ELOCTATE®, RECOMBINATE®, KOGENATE FS®, HELIXATE® Fs, HELIXATE®, XYNTHA®/REFACTO AB®, HEMOFIL-M®, MONARC M®, ALPHANATE®, KOATE-DVI®, NUWIQ® or HYATE: C®), Factor IX (e.g., a plasma derived Factor IX product such as, BERININ® P, MONOFIX® or MONONINE®; or a recombinant Factor IX product such as ALPHANINE SD®, ALPROLIX®, BEBULIN®, BEBULIN VH®, BENEFIX®, IXINITY®, PROFILNINE SD®, PROPLEX T®, or RIXUBIS®), Factor X, Factor XI, Factor XII and Factor XIII (e.g., FIBROGAMMIN® P, CORIFACT®, CLUVOT® or CLUVIAT®). In one example, the therapeutic protein is a von Willebrand Factor/FVIII complex (e.g., HUMATE-P®, HAEMATE®-P, BIOSTATE® or VONCENTO®). In an alternative example, the therapeutic protein is a prothrombin complex (e.g., BERIPLEX® P/N, CONFIDEX® or KCENTRA®). In another example, the therapeutic protein is a fibrinogen (e.g., RIASTAP®, HAEMOCOMPLETTAN® P). In one example, the therapeutic protein is a modified form of a coagulation factor, e.g., as described herein.

As will be apparent from the foregoing, the present disclosure provides methods of concomitant therapeutic treatment of a subject, comprising administering to a subject in need thereof an effective amount of a first agent and a second agent, wherein the first agent is a serum albumin conjugate of the present disclosure, and the second agent is also for the prevention or treatment of a bleeding disorder.

As used herein, the term "concomitant" as in the phrase "concomitant therapeutic treatment" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agent, wherein the second or additional agent, for example, may have been previously administered. A concomitant therapeutic treatment may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human)

The optimum concentration of the active ingredient(s) in the chosen medium can be determined empirically, according to procedures known to the skilled artisan, and will depend on the ultimate pharmaceutical formulation desired.

The dosage ranges for the administration of the serum albumin conjugate of the disclosure are those large enough to produce the desired effect. For example, the composition comprises an effective amount of the serum albumin conjugate. In one example, the composition comprises a therapeutically effective amount of the serum albumin conjugate. In another example, the composition comprises a prophylactically effective amount of the serum albumin conjugate.

The dosage should not be so large as to cause adverse side effects, such as paradoxical bleedings and development of inhibitors. Generally, the dosage will vary with the age, condition, sex and extent of the disease in the patient and can be determined by one of skill in the art. The dosage can be adjusted by the individual physician in the event of any complication.

Dosage can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

In some examples, the serum albumin conjugate is administered at an initial (or loading) dose which is higher than subsequent (maintenance doses). For example, the v is administered at an initial dose of between about 10 mg/kg to about 30 mg/kg. The binding protein is then administered at a maintenance dose of between about 0.0001 mg/kg to about 10 mg/kg. The maintenance doses may be administered every 7-35 days, such as, every 7 or 14 or 28 days.

In some examples, a dose escalation regime is used, in which a serum albumin conjugate is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

A subject may be retreated with the serum albumin conjugate, by being given more than one exposure or set of doses, such as at least about two exposures of the binding protein, for example, from about 2 to 60 exposures, and more particularly about 2 to 40 exposures, most particularly, about 2 to 20 exposures.

In one example, any retreatment may be given when signs or symptoms of disease return, e.g., a bleeding episode.

In another example, any retreatment may be given at defined intervals. For example, subsequent exposures may be administered at various intervals, such as, for example, about 24-28 weeks or 48-56 weeks or longer. For example, such exposures are administered at intervals each of about 24-26 weeks or about 38-42 weeks, or about 50-54 weeks.

In the case of a subject that is not adequately responding to treatment, multiple doses in a week may be administered. Alternatively, or in addition, increasing doses may be administered.

In another example, for subjects experiencing an adverse reaction, the initial (or loading) dose may be split over numerous days in one week or over numerous consecutive days.

Administration of a serum albumin conjugate according to the methods of the present disclosure can be continuous or intermittent, depending, for example, on the recipient's physiological condition, whether the purpose of the administration is therapeutic or prophylactic, and other factors known to skilled practitioners. The administration may be essentially continuous over a preselected period of time or may be in a series of spaced doses, e.g., either during or after development of a condition.

Kits and Other Compositions of Matter

Another example of the disclosure provides kits containing a serum albumin conjugate of the present disclosure useful for the treatment or prevention of a bleeding disorder as described above.

In one example, the kit comprises (a) a container comprising a serum albumin conjugate optionally in a pharmaceutically acceptable carrier or diluent; and (b) a package insert with instructions for treating or preventing a bleeding disorder in a subject.

In one example, the kit comprises (a) at least one serum albumin conjugate; (b) instructions for using the kit in treating or preventing the bleeding disorder in the subject; and (c) optionally, at least one further therapeutically active compound or drug.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating or preventing a bleeding disorder and may have a sterile access port (for example, the container may be an intravenous solution bag or a vial having a stopper pierceable by a hypodermic injection needle). At least one active agent in the composition is the serum albumin conjugate. The label or package insert indicates that the composition is used for treating a subject eligible for treatment, e.g., one having or predisposed to developing a bleeding disorder, with specific guidance regarding dosing amounts and intervals of the serum albumin conjugate and any other medicament being provided.

The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The kit optionally further comprises a container comprises a second medicament, wherein the serum albumin conjugate is a first medicament, and which article further comprises instructions on the package insert for treating the subject with the second medicament, in an effective amount. The second medicament may be a therapeutic protein set forth above.

The present disclosure includes the following non-limiting Examples.

EXAMPLES

Example 1: Generation of Human Serum Albumin Variants

A library of randomly-mutated variants of human serum albumin (HSA) was generated using standard error-prone PCR of human serum albumin Truncation and frameshift variants were removed using intein-based open reading frame (ORF) selection, as previously described in Gerth et al. (Protein Eng Des Sel 2004 17 (7):595-602).

HSA variant clones were then subcloned and transfected into Flp-In™ CHO cells (Invitrogen) to generate a library of transfected stable cell lines, each containing a single copy of a mutant albumin fusion protein. Briefly, a Flp-In™ CHO host cell line containing an integrated Flp recombination target (PRT) site was obtained. The library of HSA variants was cloned into the pcDNA5/FRT expression plasmid in frame with the platelet derived growth factor receptor (PDGFR) transmembrane domain and a Myc tag, under the control of the human CMV promoter. The pcDNA5/FRT vector containing the HSA library and a pOG44 plasmid, which constitutively expresses the Flp recombinase under the control of the human CMV promoter, were co-transfected into the Flp-In™ host cell line, resulting in all transfected cells that successfully underwent Flp-catalysed recombination harboring one copy of the mutant albumin fusion protein. Expression of the HSA variants as fusion proteins with the PDGFR transmembrane region allowed extracellular display of membrane-tethered variants on the surface of mammalian cells. Stably transfected cells were grown for approximately 14 days in selection media to remove non-transfected cells.

Example 2: Identification of Residues Associated with Increased Affinity for FcRn/β2m To determine the binding affinity of the HSA variants to neonatal Fc receptor (FcRn/β2m), individual pools of CHO cells stably expressing HSA variants were stained with alexa-488 labeled FcRn/β2m (10 μg/ml at pH5.4 and 100 μg/ml at pH7.3; to detect target binding) and anti-myc-alexa 647 (to detect expression of the construct) at pH 5.4 and pH 7.3 and analysed by flow cytometry. The amount of labelled FcRn bound to cells expressing each HSA variant was quantified as the geometric mean fluorescence intensity (geoMFI) data of the stained cells, background fluorescence due to non-specific binding of the labelled FcRn to the cells was subtracted and relative binding to FcRn/β2m was determined compared to wild-type HSA and HSA variant K573Y (described in Anderson et al. (2014) J Biol Chem, 289: 13492).

Two clones (clone 3.9 and clone 5.6) were selected for further analysis based on affinity and individual mutations within each clone were dissected out to determine the contribution of each mutation to the overall affinity of the parent clone.

FcRn binding to each of the HSA variants was measured by flow cytometry in two independent experiments. The amount of labelled FcRn bound to cells expressing a HSA variant was quantified as the geometric mean fluorescence intensity (geoMFI) of the stained cells. Background fluorescence due to non-specific binding of the labelled FcRn to the cells was subtracted from the value obtained. Improved binding to FcRn/β2m over wild-type was observed at pH5.4 for positive control HSA variant K573Y, as well as HSA variants with the single substitutions Q522L, G572R and A552V. As shown in Table 1, a number of clones showed no improvement in binding over wild-type, including T133I, K162N, K317E, F377I, I388T, F157L, P282S and Y452S. None of the clones showed any appreciable binding to FcRn/β2m at pH 7.3.

Example 3: Generation of HSA Variants with Single Amino Acid Substitutions

Amino acid residues Q522, G572 and A552 were selected as residues of interest. A panel of HSA variants was generated with single substitution of every amino acid, except cysteine, at residue Q522 or G572 and stably expressed in CHO cells. Binding of HSA variants to FcRn/β2m was determined as described above by flow cytometry in four independent experiments. The amount of labelled FcRn bound to cells expressing each HSA variant was quantified as the geometric mean fluorescence intensity (geoMFI) data of the stained cells. Background fluorescence due to non-specific binding of the labelled FcRn to the cells was subtracted and upper and lower confidence intervals (95% CI) for each experimentally determined mean value calculated.

The FcRn binding intensity (geoMFI) of all HSA variants at both pH 5.5 and pH 7.4 was normalized separately to adjust for systematic differences in measured intensities between experiments. For both pH conditions the replicate measurements of the binding of a given HSA variant were adjusted to a mean value across replicates (similar to intensity normalization of microarray data as described in Dudoit et al. 2002 Statistica Sinica 12, 111-139). For measurement of FcRn binding at pH 5.5, the replicates had clear non-linear differences across the range of geoMFI values measured for all the tested variants. Quadratic functions were fit by robust regression to each replicate's binding strength versus the mean (across the 4 replicates) binding strength, with all geoMFI values on a log 2 scale. Through the adjustment, each predicted experiment-specific binding strength was replaced by the across-experiments mean binding strength, while each variant's residual remained the same. For measurement of FcRn binding at pH 7.4, linear functions were fit (i.e., the adjustment step is equivalent to subtracting an experiment specific (small) intercept constant plus dividing by an experiment specific scaling constant).

Nine Q522 variants demonstrated statistically significant increased FcRn/β2m binding at acidic pH 5.5: Q522G, Q522I, Q522K, Q522M, Q522F, Q522W, Q522Y, Q522V and Q522L relative to wild-type HSA (Table 2). Six G572 variants demonstrated statistically significant increased FcRn/β2m binding at acidic pH 5.5: G572A, G572E, G572H, G572S, G572K and G572R relative to wild-type HSA (Table 3). No significant binding of any of the HSA variants to FcRn/β2m was observed at pH 7.4. Substitutions at Q522L, A552V, G572R and K573Y showed the most significant increase in binding to FcRn/β2m at acidic pH 5.5 (Table 4) relative to wild-type HSA.

Example 4: Generation of HSA Variants with Multiple Amino Acid Substitutions

To test the additive or synergistic effects of the mutations on FcRn/β2m binding, HSA variants harboring double, triple and quadruple amino acid substitutions were generated as previously described.

As shown in Table 5, double HSA variants Q522L/A552V, Q522L/G572R and A552V/G572R demonstrated significantly improved FcRn/β2m binding at pH5.5 over wild-type HSA and corresponding HSA variants with single amino acid substitutions.

Double HSA variants harboring the K573Y mutation (Q522L/K573Y, A552V/K573Y and G572R/K573Y) showed significantly improved FcRn/β2m binding at pH5.5 over wild-type HSA and the single HSA variants Q522L A552V, G572R. Double HSA variants Q552L/K573Y and A552V/K573Y but not G572R/K573Y also showed significantly improved FcRn/β2m binding at pH5.5 over HSA variant K573Y.

Triple HSA variant Q522L/A522V/G572R demonstrated significantly improved FcRn/β2m binding at pH5.5 over wild-type HSA and corresponding HSA variants with single and double amino acid substitutions, as well as approximately twice the level of binding compared to HSA variant K573Y (Table 5).

Triple HSA variants Q522L/A552V/K573Y and Q522L/G572R/K573Y demonstrated significantly improved FcRn/β2m binding at pH5.5 over wild-type HSA and corresponding HSA variants with single amino acid substitutions, as well as significantly improved binding over HSA variant K573Y.

Quadruple HSA variant Q522L/A552V/G572R/K573Y demonstrated significantly improved FcRn/β2m binding at pH5.5 over wild-type HSA and corresponding HSA variants with single amino acid substitutions. However, the quadruple variant also demonstrated significantly increased FcRn/β2m binding at pH7.4 over wild-type HSA.

Example 5: Binding Kinetics of HSA Variants with Single, Double and Triple Amino Acid Substitutions To test the effects of the mutations on FcRn/β2m binding, single, double and triple HSA variants were generated as previously described. Binding kinetics were measured using SPR with BIAcore™ 4000 (GE Healthcare Life Sciences). Recombinant hFcRn/β2M was chemically biotinylated and tethered to a GE streptavidin sensor chip (GE Healthcare Life Sciences). Briefly, human FcRn/β2M was chemically modified at a low protein:biotin ratio in PBS (i.e., minimal biotinylation) using an extended biotin linker (Sulfo-NHS-LC-LC-Biotin) prepared at 1:0.25 molar ratio on ice for 2 hours. The reaction mix was desalted using a spin column (10000 NMW) according to the manufacturer's instructions.

HSA variants were injected at concentrations of 5, 1.7, 0.6 and 0 μM. Assays were performed in 10 mM HEPES; 150 mM NaCl pH 6.0 at 37° C. in quadruplicate. The association and dissociation phases were monitored for 100 seconds and each cycle ended with a regeneration step at neutral, pH 7.4 for 90 seconds. Sensograms were double-subtracted from the reference (spot 3) and blank buffer injections within each run.

Rate constants and overall affinity rates were obtained for all HSA variants screened against minimally biotinylated human FcRn at pH 6. Data obtained from 1.7 μM and 0.6 μM injections fit well to a 1:1 binding model while data acquired from 5 μM injections were used for model fitting due to saturated responses.

As shown in Table 6, eight Q522 variants demonstrated increased FcRn/β2m binding at acidic pH 6.0: Q522F, Q522G, Q522M, Q522K, Q522Y, Q522I, Q522A and Q522L relative to wild-type HSA. Six G572 variants demonstrated increased FcRn/β2m binding at acidic pH 6.0: G572R, G572K, G572V, G572A, G572S and G572H relative to wild-type HSA (Table 6). Double HSA variants A522V/G572R, Q522L/A552V and triple HSA variant Q522L/A552V/G572R all demonstrated increased FcRn/β2m binding at acidic pH 6.0 relative to wild-type HSA (Table 6).

Example 6: Binding Kinetics of HSA Variants with Single, Double and Triple Amino Acid Substitutions Binding kinetics of single, double and triple HSA variants on FcRn/β2m binding was measured using SPR with BIA- CORE™ 8000 (GE Healthcare Life Sciences). HSA [H464Q] used as negative control.

Recombinant hFcRn/β2M was chemically biotinylated and tethered to GE's streptavidin sensor chip as described above. HSA variants were injected at concentrations ranging from 2 to 0.015 μM. Assay was performed in 10 mM HEPES; 150 mM NaCl (pH 6.0) at 37° C. in triplicate. The association phase was monitored for 120 seconds and the dissociation for 240 seconds. Each cycle ended with a regeneration step under basic conditions (i.e. pH 8.0) for 90 seconds. Sensograms were double-subtracted from the reference and blank buffer injections within each run.

Data obtained under acidic conditions fit well to a 1:1 binding model. Rate constants and binding affinity were established as previously described.

As shown in Table 7, the majority of HSA mutants showed improvement (up to 3-fold) in binding affinity (KD) compared to the wild type HSA. Double HSA variants [Q522L/A552V], [Q522L/G572R] and [A552V/G572R] showed up to 10-fold improved binding affinity to hFcRn/β2m compared to recombinant wild-type HSA. Triple HSA variant [Q522L/A552V/G572R] had the strongest binding, at approximately 25 nM. Negative control HSA [H464Q] did not bind hFcRn/β2m.

Example 7: Binding Affinity of Select HSA Variants to Mammalian Fc12n/β2m at Acidic and Neutral pH Single HSA variants G572R and K573Y, double HSA variants Q522L/A552V, Q522L/G572R and A552V/G572R and triple HSA variant Q522L/A552V/G572R were generated as previously described and binding kinetics measured using SPR with BIACORE™ 4000 (GE Healthcare Life Sciences).

HSA variants were diluted to 1 μg/mL and directly immobilized on two surface sites of a carboxymethyl dextran (CM-5) sensor chip (GE Healthcare Life Sciences) using amine-coupling chemistry (NHS/EDC). HSA variants were immobilised to values between 100 and 500RU in the outer spot (1 and 5) and 200 to 1000 RU in the inner spot (2 and 4) of each flow cell. Spot 3 of each flow cell was activated/deactivated and used for reference subtraction. The flow rate of FcRn/β2m was kept constant at 30 μL/min The binding of soluble recombinant human, cynomolgus monkey ('cyno'), rat and mouse FcRn/β2m to immobilized HSA variants was tested at acidic (pH 6.0) and neutral pH (pH7.3). A concentration range of 2 to 0.007 μM (pH6.0) and 20 to 0.078 μM (pH7.3) was used and association and dissociation phases were monitored for 180 and 600 seconds respectively.

Regeneration of the surface was performed as previously described. Sensogram data obtained at acidic conditions fitted well to a 1:1 binding model. However, sensograms obtained at pH 7.3 showed off-rates near the limit of detection of the instrument, requiring a steady-state binding model for analysis.

As shown in Table 8, at pH 6.0 human and cyno FcRn/β2m showed nanomolar binding affinity. Human and cyno FcRn/β2m showed near 20-fold improved affinity for HSA K573Y and 5-fold improved affinity for HSA G572R compared to wild-type HSA at pH 6. The affinity of double HSA variants Q522L/A552V, Q522L/G572R and A552V/G572R was about 50 nM, about 27 nM and about 27 nM to human FcRn/β2m, respectively, and about 84 nM, 49 nM and 48 nM to cyno FcRn/β2m, respectively.

In comparison, rat and murine FcRn/β2m showed weak to no binding under the same conditions. Rat FcRn/β2m showed 100-fold weaker affinity to HSA variants and no binding to wild-type HSA, HSA variant Q522L/A552V and HSA variant G572R. Rat FcRn/β2m bound HSA K573Y at approximately 1 μM under these conditions but no binding was detected for HSA G572R. Mouse FcRn/β2m did not bind any of the HSA variants tested.

As shown in Table 8, at pH 7.3 human and cyno FcRn/β2m did not bind wild-type HSA and showed weak binding (>50 μM) to HSA K573Y at pH7.3. Binding affinity to other HSA variants ranged from 7 to 63 μM. Rat and murine FcRn/β2m did not bind any of the HSA variants tested at pH 7.3.

Example 8: Pharmacokinetic (PK) Properties of HSA Variants in Mice Expressing Human FcRn To assess the PK properties of the HSA variants, transgenic mice expressing human FcRn receptor ("hFcRn Tg32" homozygous mice (i.e., B6.Cg-FcgrttmlDcr Tg(FCGRT) 32Dcr/DcrJ) were used. Animals of mixed sex and age (10-14 weeks old; 3 animals per time point) were intravenously injected with 10 mg/kg of wild-type HSA, single HSA variant K573Y, double HSA variant Q522L/A552V or triple HSA variant Q522L/A552V/G572R.

Blood was collected and plasma levels of human serum albumin assessed using a human albumin ELISA kit (Bethyl Laboratories, cat no. E88-129) according to the manufacturer's instructions with the exception of using each test article to generate an individual reference curve. Data was averaged for each time point prior to analysis and data was analysed by non-linear (Marquandt-Levenberg) minimisation fitting using a custom MATLAB program NCAPKfit. Model fitting was done with 1/Y^2 weighting fitting using least squares and the equation used was:

$$PK2(t)=A*\exp(-\log(2)*t/T1)+B*\exp(-\log(2)*t/T2).$$

Mean residence time (MRT), area under the curve (AUC) and clearance rates were calculated using standard statistical formulae.

As shown in FIG. 1, Table 9 and Table 10 below, the pharmacokinetic properties of wildtype HSA were significantly different from all three HSA variants, with wildtype HSA having shorter mean residence time (MRT), smaller area under the curve (AUC) and faster clearance. Single HSA variant K573Y, double HSA variant Q522L/A552V and triple HSA variant Q522L/A552V/G572R all had significantly better pharmacokinetics by all three criteria (i.e., MRT, AUC and clearance) compared to the wildtype HSA.

TABLE 1

Binding of FcRn-alexa488 to HSA variants at pH 5.4 (10 µg/mL FcRn-alexa488) and pH 7.3 (100 µg/mL FcRn-alexa488)

| HSA variant | pH 5.4 geoMFI | pH 5.4 Fold change to WT | pH 7.3 geoMFI | pH 7.3 Fold change to WT |
|---|---|---|---|---|
| Clone 5.6 | | | | |
| HSA [T133I/K162N/N295I/Q522L] (clone 5.6) | 15931.6 | 9.5 | 24.6 | 1.5 |
| HSA [T133I/K162N/Q522L] | 15090.6 | 9.0 | 23 | 1.4 |
| HSA [T133I/Q522L] | 10839.6 | 6.5 | 20.1 | 1.2 |
| HSA [T133I] | 1265.6 | 0.8 | 18.9 | 1.2 |
| HSA [K162N] | 1437.6 | 0.9 | 17.4 | 1.1 |
| HSA [Q522L] | 16468.6 | 9.8 | 17.4 | 1.1 |
| HSA [WT] | 1674.6 | 1.0 | 16.3 | 1.0 |
| HSA [K573Y] | 45011.6 | 26.9 | 15.6 | 1.0 |
| Clone 3.9 | | | | |
| HSA [K317E/M329V/K372E/F377I/I388T/A552V/G572R] (clone 3.9) | 34796.6 | 20.8 | 28.8 | 1.8 |
| HSA [K317E/K372E/A552V/G572R] | 29479.6 | 17.6 | 29.6 | 1.8 |
| HSA [T133I/Q522L/A552V/G572R] | 37814.6 | 22.6 | 53.8 | 3.3 |
| HSA [K317E] | 1374.6 | 0.8 | 23.9 | 1.5 |
| HSA [M329V] | 1329.6 | 0.8 | 18.7 | 1.1 |
| HSA [K372E] | 1469.6 | 0.9 | 21.7 | 1.3 |
| HSA [F377I] | 1483.6 | 0.9 | 9.5 | 0.6 |
| HSA [I388T] | 3444.6 | 2.1 | 13.9 | 0.9 |
| HSA [A552V] | 8082.6 | 4.8 | 17.5 | 1.1 |
| HSA [G572R] | 11924.6 | 7.1 | 21.6 | 1.3 |
| HSA [A552V/G572R] | 30527.6 | 18.2 | 32 | 2.0 |
| HSA [WT] | 1674.6 | 1.0 | 16.3 | 1.0 |
| HSA [K573Y] | 45011.6 | 26.9 | 15.6 | 1.0 |

TABLE 2

Mean and range (95% confidence interval) of binding of FcRn-alexa488 to HSA variants at pH 5.5 and pH 7.4.

| HSA variant | pH 5.5 Mean geoMFI (95% CI) | pH 5.5 P value | pH 5.5 Fold change to WT (95% CI) | pH 7.4 Mean geoMFI (95% CI) | pH 7.4 P value | pH 7.4 Fold change to WT (95% CI) |
|---|---|---|---|---|---|---|
| HSA[Q522A] | 170.9 (133.5-218.8) | ns | 1.07 (0.8-1.4) | 17.8 (5.8-54.7) | ns | 0.45 (0.1-1.4) |
| HSA[Q522R] | 386.3 (253.2-589.4) | ns | 2.42 (1.6-3.7) | 17.8 (4.0-78.7) | ns | 0.45 (0.1-2.0) |
| HSA[Q522N] | 153.8 (131.3-180.3) | ns | 0.97 (0.8-1.1) | 31.4 (18.4-53.6) | ns | 0.79 (0.5-1.3) |
| HSA[Q522D] | 316.6 (262.3-382.1) | ns | 1.99 (1.6-2.4) | 22.4 (14.7-34.2) | ns | 0.56 (0.4-0.9) |
| HSA[Q522E] | 127.9 (92.6-176.6) | ns | 0.8 (0.6-1.1) | 29.2 (15.5-55.0) | ns | 0.73 (0.4-1.4) |
| HSA[Q522G] | 383.9 (317.9-463.6) | (1) | 2.41 (2.0-2.9) | 26.4 (7.5-92.8) | ns | 0.66 (0.2-2.3) |
| HSA[Q522H] | 147.7 (132.5-164.8) | ns | 0.93 (0.8-1.0) | 27.2 (11.7-62.9) | ns | 0.68 (0.3-1.6) |
| HSA[Q522I] | 666.3 (544.3-815.6) | (1) | 4.18 (3.4-5.1) | 26.3 (4.8-144.7) | ns | 0.66 (0.1-3.6) |
| HSA[Q522K] | 452 (356.2-573.6) | (1) | 2.84 (2.2-3.6) | 30.4 (9.9-93.8) | ns | 0.77 (0.2-2.4) |
| HSA[Q522M] | 586.3 (511.7-671.8) | (1) | 3.68 (3.2-4.2) | 38 (20.8-69.5) | ns | 0.96 (0.5-1.7) |
| HSA[Q522F] | 1379.6 (1069.9-1779.1) | (2) | 8.66 (6.7-11.2) | 27.9 (8.4-93.0) | ns | 0.7 (0.2-2.3) |
| HSA[Q522P] | 169.4 (144.9-198.1) | ns | 1.06 (0.9-1.2) | 29.4 (10.2-85.4) | ns | 0.74 (0.3-2.1) |
| HSA[Q522S] | 257.6 (218.9-303.1) | ns | 1.62 (1.4-1.9) | 32.7 (10.9-98.0) | ns | 0.82 (0.3-2.5) |
| HSA[Q522T] | 290.3 (239.0-352.6) | ns | 1.82 (1.5-2.2) | 28.3 (10.3-77.7) | ns | 0.71 (0.3-2.0) |
| HSA[Q522W] | 596.2 (406.4-874.6) | (1) | 3.74 (2.5-5.5) | 20.2 (6.5-62.3) | ns | 0.51 (0.2-1.6) |
| HSA[Q522Y] | 1213.6 (1074.5-1370.7) | (2) | 7.61 (6.7-8.6) | 18.6 (4.9-71.3) | ns | 0.47 (0.1-1.8) |
| HSA[Q522V] | 617 (477.6-797.0) | (1) | 3.87 (3.0-5.0) | 32.8 (14.0-76.9) | ns | 0.82 (0.4-1.9) |
| HSA[Q522L] | 2203.6 (1689.9-2873.3) | (2) | 13.83 (10.6-18.0) | 30.3 (10.8-85.1) | ns | 0.76 (0.3-2.1) |
| HSA WT | 159.4 (85.6-296.7) | n/a | 1.0 | 39.8 (16.9-93.3) | n/a | 1.0 |
| HSA [K573Y] | 29147.9 (20225.5-42006.2) | (2) | 182.89 (126.9-263.6) | 27.6 (12.8-59.7) | ns | 0.7 (0.3-1.5) |

(1) Significant difference (p < 0.01) from HSA WT;
(2) Significant difference (p < 0.001) from HSA WT;
ns = not significantly greater than wild-type HSA.
n/a = not applicable

TABLE 3

Mean and range (95% confidence interval) of binding of FcRn-alexa488 to HSA variants at pH 5.5 and pH 7.4.

| | pH 5.5 | | | pH 7.4 | | |
|---|---|---|---|---|---|---|
| HSA variant | Mean geoMFI (95% CI) | P value | Fold change to WT (95% CI) | Mean geoMFI (95% CI) | P value | Fold change to WT (95% CI) |
| HSA[G572A] | 536.4 (419.3-686.3) | (1) | 3.37 (2.6-4.3) | 29.8 (16.0-55.7) | ns | 0.75 (0.4-1.4) |
| HSA[G572N] | 85.8 (42.0-175.6) | ns | 0.54 (0.3-1.1) | 36.4 (19.9-66.7) | ns | 0.92 (0.5-1.7) |
| HSA[G572D] | 304.9 (235.1-395.5) | ns | 1.91 (1.5-2.5) | 32.7 (16.8-63.9) | ns | 0.82 (0.4-1.6) |
| HSA[G572Q] | 200.8 (108.3-372.3) | ns | 1.26 (0.7-2.3) | 40.2 (23.5-68.7) | ns | 1.01 (0.6-1.7) |
| HSA[G572E] | 378.7 (298.2-480.8) | (1) | 2.38 (1.9-3.0) | 28.8 (12.5-66.6) | ns | 0.72 (0.3-1.7) |
| HSA[G572H] | 495.1 (356.3-687.9) | (1) | 3.11 (2.2-4.3) | 33.5 (13.5-83.4) | ns | 0.84 (0.3-2.1) |
| HSA[G572I] | 35.2 (13.7-90.5) | ns | 0.22 (0.1-0.6) | 28.9 (11.2-74.7) | ns | 0.73 (0.3-1.9) |
| HSA[G572L] | 31.2 (7.4-131.1) | ns | 0.2 (0.05-0.8) | 20.3 (11.4-36.0) | ns | 0.51 (0.3-0.9) |
| HSA[G572K] | 9200.8 (5674.0-14919.5) | (2) | 57.73 (35.6-93.6) | 22.7 (12.9-39.7) | ns | 0.57 (0.3-1.0) |
| HSA[G572M] | 38.2 (6.7-218.8) | ns | 0.24 (0.04-1.4) | 24 (13.1-44.1) | ns | 0.6 (0.3-1.1) |
| HSA[G572F] | 25.7 (6.4-103.5) | ns | 0.16 (0.04-0.6) | 20.6 (10.3-41.2) | ns | 0.52 (0.3-1.0) |
| HSA[G572P] | 215.9 (20.5-2276.5) | ns | 1.35 (0.1-14.3) | 30.6 (18.9-49.7) | ns | 0.77 (0.5-1.2) |
| HSA[G572S] | 445.1 (390.5-507.3) | (1) | 2.79 (2.5-3.2) | 18.4 (8.4-40.6) | ns | 0.46 (0.2-1.0) |
| HSA[G572T] | 38 (18.1-79.8) | ns | 0.24 (0.1-0.5) | 18.1 (4.4-74.4) | ns | 0.46 (0.1-1.9) |
| HSA[G572W] | 34.4 (16.4-71.9) | ns | 0.22 (0.1-0.5) | 21.2 (8.4-53.6) | ns | 0.53 (0.2-1.3) |
| HSA[G572Y] | 39 (15.9-95.5) | ns | 0.24 (0.1-0.6) | 29.9 (14.4-62.1) | ns | 0.75 (0.4-1.6) |
| HSA[G572V] | 58.2 (47.3-71.6) | ns | 0.37 (0.3-0.4) | 20.7 (8.3-51.3) | ns | 0.52 (0.2-1.3) |
| HSA[G572R] | 6814.2 (4453.0-10427.3) | (2) | 42.76 (27.9-65.4) | 31.7 (12.0-84.3) | ns | 0.8 (0.3-2.1) |
| HSA WT | 159.4 (85.6-296.7) | n/a | 1.0 | 39.8 (16.9-93.3) | n/a | 1.0 |
| HSA [K573Y] | 29147.9 (20225.5-42006.2) | (2) | 182.89 (126.9-263.6) | 27.6 (12.8-59.7) | ns | 0.7 (0.3-1.5) |

(1) Significant difference (p < 0.01) from HSA WT;
(2) Significant difference (p < 0.001) from HSA WT;
ns = not significantly greater than wild-type HSA.
n/a = not applicable

TABLE 4 mean and range (95% confidence interval) of binding of FcRn-alexa488 to HSA mutants at pH 5.5 and pH 7.4

| | pH 5.5 | | | pH 7.4 | | |
|---|---|---|---|---|---|---|
| HSA variant | Mean geoMFI (95% CI) | P value | Fold change to WT (95% CI) | Mean geoMFI (95% CI) | P value | Fold change to WT (95% CI) |
| HSA WT | 159.4 (85.6-296.7) | n/a | 1.0 | 39.8 (16.9-93.3) | n/a | 1.0 |
| HSA [K573Y] | 29147.9 (20225.5-42006.2) | (2, 3, 4, 5) | 182.89 (126.9-263.6) | 27.6 (12.8-59.7) | ns | 0.7 (0.3-1.5) |
| HSA[Q522L] | 2203.6 (1689.9-2873.3) | (2, 4) | 13.83 (10.6-18.0) | 30.3 (10.8-85.1) | ns | 0.76 (0.3-2.1) |
| HSA[A552V] | 644 (464.3-893.4) | (1) | 4.04 (2.9-5.6) | 46.1 (36.2-58.7) | ns | 1.16 (0.9-1.5) |
| HSA[G572R] | 6814.2 (4453.0-10427.3) | (2, 3, 4) | 42.76 (27.9-65.4) | 31.7 (12.0-84.3) | ns | 0.8 (0.3-2.1) |
| HSA[Q522L, A552V] | 7572.3 (6586.9-8705.1) | (2, 3, 4) | 47.51 (41.3-54.6) | 28.8 (12.5-66.4) | ns | 0.73 (0.3-1.7) |
| HSA[Q522L, G572R] | 28723.1 (19498.2-42312.3) | (2, 3, 4, 5) | 180.23 (122.3-265.5) | 37.6 (19.8-71.4) | ns | 0.95 (0.5-1.8) |
| HSA[A552V, G572R] | 37739.5 (35785.0-39800.7) | (2, 3, 4, 5) | 236.8 (224.5-249.7) | 37.9 (24.3-59.1) | ns | 0.95 (0.6-1.5) |
| HSA[Q522L, A552V, G572R] | 65180.1 (54138.9-78473.1) | (2, 3, 4, 5, 6) | 408.98 (339.7-492.4) | 46.8 (33.6-65.3) | ns | 1.18 (0.8-1.6) |

(1) Significant difference (p < 0.01) from HSA WT (2) Significant difference (p < 0.001) from HSA WT (3) Significant difference (p < 0.001) from HSA[Q522L]

(4) Significant difference (p < 0.001) from HSA[A552V]

(5) Significant difference (p < 0.001) from HSA[G572R]

(6) Significant difference (p < 0.001) from HSA[K573Y]

ns = not significantly greater than wild-type HSA n/a = not applicable

TABLE 5

Mean and range (95% confidence interval) of binding of FcRn-alexa488 to HSA mutants at pH 5.5 and pH 7.4.

| HSA variant | pH 5.5 Mean geoMFI (95% CI) | P value | Fold change to WT (95% CI) | pH 7.4 Mean geoMFI (95% CI) | P value | Fold change to WT (95% CI) |
|---|---|---|---|---|---|---|
| HSA WT | 159.4 (85.6-296.7) | n/a | 1.0 | 39.8 (16.9-93.3) | ns | 1.0 |
| HSA [K573Y] | 29147.9 (20225.5-42006.2) | (2, 3, 4, 5) | 182.89 (126.9-263.6) | 27.6 (12.8-59.7) | ns | 0.7 (0.3-1.5) |
| HSA[Q522L] | 2203.6 (1689.9-2873.3) | (2, 4) | 13.83 (10.6-18.0) | 30.3 (10.8-85.1) | ns | 0.76 (0.3-2.1) |
| HSA[A552V] | 644 (464.3-893.4) | (1) | 4.04 (2.9-5.6) | 46.1 (36.2-58.7) | ns | 1.16 (0.9-1.5) |
| HSA[G572R] | 6814.2 (4453.0-10427.3) | (2, 3, 4) | 42.76 (27.9-65.4) | 31.7 (12.0-84.3) | ns | 0.8 (0.3-2.1) |
| HSA[Q522L, A552V] | 7572.3 (6586.9-8705.1) | (2, 3, 4) | 47.51 (41.3-54.6) | 28.8 (12.5-66.4) | ns | 0.73 (0.3-1.7) |
| HSA[Q522L, G572R] | 28723.1 (19498.2-42312.3) | (2, 3, 4, 5) | 180.23 (122.3-265.5) | 37.6 (19.8-71.4) | ns | 0.95 (0.5-1.8) |
| HSA[A552V, G572R] | 37739.5 (35785.0-39800.7) | (2, 3, 4, 5) | 236.8 (224.5-249.5) | 37.9 (24.3-59.1) | ns | 0.95 (0.6-1.5) |
| HSA[Q522L, A552V, G572R] | 65180.1 (54138.9-78473.1) | (2, 3, 4, 5, 7, 8, 9, 10) | 408.98 (339.7-492.4) | 46.8 (33.6-65.3) | ns | 1.18 (0.8-1.6) |
| HSA[Q522L, K573Y] | 85950.7 (56455.2-130856.3) | (2, 3, 7) | 539.3 (354.2-821.1) | 28.3 (12.6-63.5) | ns | 0.7 (0.3-1.6) |
| HSA[A552V, K573Y] | 92717.2 (58348.7-147329.4) | (2, 4, 7) | 581.8 (366.1-924.4) | 36.5 (22.3-59.7) | ns | 0.9 (0.6-1.5) |
| HSA[G572R, K573Y] | 42587.2 (28709.3-63174.8) | (2, 5) | 267.2 (180.1-396.4) | 30.4 (13.7-67.4) | ns | 0.8 (0.3-1.7) |
| HSA[Q522L, A552V, K573Y] | 103807.3 (92277.2-116778.1) | (2, 3, 4, 7) | 651.4 (579.0-732.7) | 31.9 (16.6-61.2) | ns | 0.8 (0.4-1.5) |
| HSA[Q522L, G572R, K573Y] | 62796.1 (40576.2-97184.1) | (2, 3, 5, 6) | 394.0 (254.6-609.8) | 193.9 (166.5-225.7) | ns | 4.9 (4.2-5.7) |
| HSA[Q522L, A552V, G572R, K573Y] | 70142.8 (58098.7-84683.9) | (2, 3, 4, 5, 7) | 440.1 (364.6-531.4) | 328.9 (303.0-357.0) | (1) | 8.3 (7.6-9.0) |

(1) Significant difference (p < 0.01) from HSA WT;
(2) Significant difference (p < 0.001) from HSA WT;
(3) Significant difference (p < 0.001) from HSA[Q5221L];
(4) Significant difference (p < 0.001) from HSA[A552V];
(5) Significant difference (p < 0.001) from HSA[G572R];
(6) Significant difference (p < 0.01) from HSA[K573Y];
(7) Significant difference (p < 0.001) from HSA[K573Y];
(8) Significant difference (p < 0.001) from HSA[Q522L, A552V];
(9) Significant difference (p < 0.001) from HSA[Q522L, G572R];
(10) Significant difference (p < 0.001) from HSA[A552V, G572R];
ns = not significantly greater than wild-type HSA;
n/a = not applicable

TABLE 6

Rate constants and affinity of soluble HSA mutants to biotinylated hFcRn/β2M tethered to a Streptavidin sensor chip at acidic pH (pH 6).

| HSA variant | $k_a$ (1/Ms) | $k_d$ (1/s) | $K_D$ (nM) |
|---|---|---|---|
| HSA WT | $7.42 \times 10^4$ | $3.10 \times 10^{-2}$ | 427 ± 31 |
| HSA [Q522L, A552V, G572R] | $3.42 \times 10^4$ | $1.40 \times 10^{-3}$ | 41 ± 1 |
| HSA [K573Y] | $2.72 \times 10^4$ | $1.24 \times 10^{-3}$ | 46 ± 1 |
| HSA [A552V/G572R] | $4.66 \times 10^4$ | $2.58 \times 10^{-3}$ | 55 ± 2 |
| HSA [G572R] | $4.66 \times 10^4$ | $6.21 \times 10^{-3}$ | 133 ± 1 |
| HSA [Q522L, A552V] | $3.73 \times 10^4$ | $5.00 \times 10^{-3}$ | 134 ± 3 |
| HSA [G572K] | $4.32 \times 10^4$ | $6.64 \times 10^{-3}$ | 154 ± 4 |
| HSA [Q522F] | $3.93 \times 10^4$ | $8.19 \times 10^{-3}$ | 209 ± 8 |
| HSA [G572V] | $4.98 \times 10^4$ | $1.14 \times 10^{-2}$ | 230 ± 3 |
| HSA [Q522G] | $4.81 \times 10^4$ | $1.27 \times 10^{-2}$ | 264 ± 10 |
| HSA [Q522M] | $1.07 \times 10^4$ | $3.27 \times 10^{-2}$ | 305 ± 8 |
| HSA [Q522K] | $6.07 \times 10^4$ | $1.82 \times 10^{-2}$ | 307 ± 24 |
| HSA [G572A] | $4.91 \times 10^4$ | $1.50 \times 10^{-2}$ | 308 ± 17 |
| HSA [Q522Y] | $4.66 \times 10^4$ | $1.46 \times 10^{-2}$ | 321 ± 32 |
| HSA [A552V] | $3.67 \times 10^4$ | $1.18 \times 10^{-2}$ | 322 ± 3 |
| HSA [G572S] | $7.24 \times 10^4$ | $2.29 \times 10^{-2}$ | 334 ± 39 |
| HSA [Q522I] | $5.07 \times 10^4$ | $1.69 \times 10^{-2}$ | 338 ± 23 |
| HSA [Q522A] | $5.23 \times 10^4$ | $1.80 \times 10^{-2}$ | 348 ± 22 |
| HSA [G572H] | $6.79 \times 10^4$ | $2.39 \times 10^{-2}$ | 356 ± 44 |
| HSA [Q522L] | $4.07 \times 10^4$ | $1.26 \times 10^{-2}$ | 389 ± 194 |
| HSA [Q522V] | $1.14 \times 10^4$ | $1.00 \times 10^{-2}$ | 880 ± 44 |
| HSA [Q522W] | $2.04 \times 10^4$ | $3.02 \times 10^{-2}$ | 1506 ± 197 |

TABLE 7

Rate constants and affinity of soluble HSA mutants to biotinylated hFcRn/β2M tethered to a Streptavidin sensor chip at acidic pH (pH 6).

| HSA variant | $k_a$ (1/Ms) | $k_d$ (1/s) | $K_D$ (nM) ± SEM |
|---|---|---|---|
| HSA WT | 7.70E+04 | 3.71E-02 | 479.4 ± 64.3 |
| HSA [Q522L/A552V/G572R] | 7.01E+04 | 1.76E-03 | 25.0 ± 0.6 |
| HSA [Q522L/A552V] | 6.92E+04 | 6.78E-03 | 97.9 ± 4.8 |
| HSA [Q522L/G572R] | 8.19E+04 | 4.12E-03 | 50.2 ± 1.1 |
| HSA [A552V/G572R] | 7.63E+04 | 3.18E-03 | 41.7 ± 0.5 |
| HSA [K573Y] | 4.79E+04 | 1.63E-03 | 33.9 ± 0.6 |
| HSA [G572H] | 1.07E+05 | 4.83E-02 | 452.8 ± 36.7 |
| HSA [G572R] | 1.05E+05 | 1.08E-02 | 103.1 0.3 |
| HSA [G572K] | 1.09E+05 | 1.68E-02 | 154.4 ± 9.0 |

TABLE 7-continued

Rate constants and affinity of soluble HSA mutants to biotinylated hFcRn/β2M tethered to a Streptavidin sensor chip at acidic pH (pH 6).

| HSA variant | $k_a$ (1/Ms) | $k_d$ (1/s) | $K_D$ (nM) ± SEM |
|---|---|---|---|
| HSA [Q522F] | 6.37E+04 | 1.33E−02 | 208.3 ± 3.2 |
| HSA [A552V] | 4.38E+04 | 1.26E−02 | 286.9 ± 0.3 |
| HSA [Q522I] | 7.61E+04 | 2.52E−02 | 332.1 ± 6.0 |
| HSA [Q522L] | 5.78E+04 | 1.16E−02 | 201.0 ± 1.2 |
| HSA [Q522A] | 7.53E+04 | 3.39E−02 | 465.0 ± 35.2 |
| HSA [H464Q] | NB | NB | NB |

NB: No Binding detected

TABLE 8

Binding affinity of soluble mammalian FcRn/β2m binding to immobilised human HSA variants at acidic (pH 6.0) and neutral (pH 7.3) pH.

| | Analyte | | | | | | | |
|---|---|---|---|---|---|---|---|---|
| | pH 6.0[1] | | | | pH 7.3[2] | | | |
| Ligand HSA variant | hsFcRn* ($K_D$ nM, N = 6) | cynoFcRn ($K_D$ nM, N = 4) | ratFcRn ($K_D$ nM, N = 4) | murineFcRn ($K_D$ nM, N = 4) | hsFcRn$^\phi$ ($K_D$ μM, N = 4) | cynoFcRn ($K_D$ μM, N = 2) | ratFcRn ($K_D$ μM, N = 2) | murineFcRn ($K_D$ μM, N = 2) |
| HSA WT | 343.9 ± 36.4 | 593.6 ± 11.9 | NB | NB | NB | NB | NB | NB |
| HSA [K573Y] | 18.1 ± 1.2 | 34.7 ± 0.7 | 989.2 ± 196.2 | NB | >50 | 45.2 | NB | NB |
| HSA [G572R] | 58.3 ± 2.7 | 109.1 ± 9.5 | NB | NB | 32.7 ± 3.9 | 21.1 | NB | NB |
| HSA [Q522L, A552V] | 50.1 ± 1.6 | 84.6 ± 5.1 | NB | NB | >50 | 33.0 | NB | NB |
| HSA [Q522L, G572R] | 27.8 ± 0.6 | 49.5 ± 0.7 | 4754.1 ± 354.7 | NB | 18.0 ± 1.0 | 10.7 | NB | NB |
| HSA [A552V, G572R] | 27.1 ± 0.7 | 48.4 ± 0.8 | 4823.3 ± 307.3 | NB | 20.5 ± 0.4 | 13.2 | NB | NB |
| HSA [Q522L, A552V, G572R] | 16.9 ± 0.5 | 24.5 ± 0.2 | 2245.5 ± 119.1 | NB | 16.1 ± 1.6 | 7.6 | NB | NB |

[1]Mean ± SEM values indicated in nanomolar calculated from 1:1 binding model.
[2]Human FcRn-β2m data (hsFcRn) are indicated as Mean ± SEM; cyno FcRn-β2m represent the average of two experimental replicates. KD values were calculated from sensogram data fit to a 1:1 steady-state model
*Human soluble FcRns (hsFcRn);
NB, Non-binder.

TABLE 9

Serum concentration (μg/mL; mean ± SEM) of HSA variants in transgenic mice expressing human FcRn receptor

| Days | HSA WT | HSA [Q522L, A552V] | HSA [Q522L, A552V, G572R] | HSA [573Y] |
|---|---|---|---|---|
| 0 | | | | |
| 0.042 | | | | |
| 0.25 | | | | |
| 1 | | | | |
| 2 | | | | |
| 3 | | | | |
| 4 | | | | |
| 5 | | | | |
| 7 | | | | |
| 16 | | | | |
| 21 | | | | |
| 29 | | | | |

TABLE 10

Pharmacokinetics analysis of the serum concentration of HSA variants in transgenic mice expressing human FcRn receptor.

Area Under the Curve

| HSA variant | AUC (μg/mL*d) | SD | N | p value |
|---|---|---|---|---|
| HSA WT | 344.6 | 18.2 | 3 | |
| HSA [K573Y] | 574.8 | 30 | 3 | <0.0001 |
| HSA [Q522L, A552V] | 597 | 26.2 | 3 | <0.0001 |
| HSA [Q522L, A552V, G572R] | 618 | 29 | 3 | <0.0001 |

Mean Residence Time

| HSA variant | MRT (days) | SD | N | p value |
|---|---|---|---|---|
| HSA WT | 3.31 | 0.08 | 3 | |
| HSA [K573Y] | 4.83 | 0.15 | 3 | <0.0001 |
| HSA [Q522L, A552V] | 5.06 | 0.12 | 3 | <0.0001 |
| HSA [Q522L, A552V, G572R] | 5.02 | 0.12 | 3 | <0.0001 |

Clearance

| HSA variant | Cl (ml/kg*d) | SD | N | p value |
|---|---|---|---|---|
| HSA WT | 29.1 | 1.5 | 3 | |
| HSA [K573Y] | 17.4 | 0.9 | 3 | <0.0001 |

TABLE 10-continued

Pharmacokinetics analysis of the serum concentration of HSA variants in transgenic mice expressing human FcRn receptor.

| | | | | | |
|---|---|---|---|---|---|
| HSA [Q522L, A552V] | 16.8 | 0.7 | 3 | <0.0001 | 5 |
| HSA [Q522L, A552V, G572R] | 16.2 | 0.8 | 3 | <0.0001 | | p values represent ANOVA analysis of difference between the selected HSA variant and WT

---

The invention claimed is:

1. A recombinant serum albumin variant, or functional fragment thereof, comprising an amino acid substitution selected from the group consisting of:
   (i) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, and valine substituted for alanine at position 552 of SEQ ID NO: 1; or
   (ii) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, and an amino acid selected from the group consisting of alanine, glutamic acid, histidine, serine, lysine and arginine substituted for glycine at position 572 of SEQ ID NO: 1; or
   (iii) valine substituted for alanine at a position corresponding to amino acid 552 of SEQ ID NO: 1, and an amino acid selected from the group consisting of alanine, glutamic acid, histidine, serine, lysine and arginine substituted for glycine at position 572 of SEQ ID NO: 1; and
   (iv) an amino acid selected from the group consisting of glycine, isoleucine, lysine, methionine, phenylalanine, tryptophan, tyrosine, valine and leucine substituted for glutamine at a position corresponding to amino acid 522 of SEQ ID NO: 1, valine substituted for alanine at position 552 of SEQ ID NO: 1, and an amino acid selected from the group consisting of alanine, glutamic acid, histidine, serine, lysine and arginine substituted for glycine at position 572 of SEQ ID NO: 1.

2. The recombinant serum albumin variant, or functional fragment thereof, of claim 1, wherein the recombinant serum albumin variant, or functional fragment thereof, binds with increased affinity to FcRn compared to a serum albumin set forth in SEQ ID NO: 1 or wherein the recombinant serum albumin variant, or functional fragment thereof, has an increased serum half-life compared to a serum albumin set forth in SEQ ID NO: 1.

3. The recombinant serum albumin variant, or functional fragment thereof, of claim 2, wherein the binding affinity is measured at acidic pH.

4. The recombinant serum albumin variant, or functional fragment thereof, according to claim 1, further comprising tyrosine substituted for lysine at a position corresponding to amino acid 573 of SEQ ID NO: 1.

5. The recombinant serum albumin variant, or functional fragment thereof, according to claim 1, comprising:
   (i) leucine substituted for glutamine at a position corresponding to amino acid 522 of SEQ ID NO: 1; and/or
   (ii) valine substituted for alanine at a position corresponding to amino acid 552 of SEQ ID NO: 1; and/or
   (iii) arginine substituted for glycine at a position corresponding to amino acid 572 of SEQ ID NO: 1.

6. The recombinant serum albumin variant, or functional fragment thereof, according to claim 1, comprising:
   (i) leucine substituted for glutamine at a position corresponding to amino acid 522 of SEQ ID NO: 1, and arginine substituted for glycine at a position corresponding to amino acid 572 of SEQ ID NO: 1; or
   (ii) leucine substituted for glutamine at a position corresponding to amino acid 522 of SEQ ID NO: 1, and valine substituted for alanine at a position corresponding to amino acid 552 of SEQ ID NO: 1; or
   (iii) valine substituted for alanine at a position corresponding to amino acid 552 of SEQ ID NO: 1, and arginine substituted for glycine at a position corresponding to amino acid 572 of SEQ ID NO: 1; or
   (iv) leucine substituted for glutamine at a position corresponding to amino acid 522 of SEQ ID NO: 1, and tyrosine substituted for lysine at a position corresponding to amino acid 573 of SEQ ID NO: 1; or
   (v) valine substituted for alanine at a position corresponding to amino acid 552 of SEQ ID NO: 1, and tyrosine substituted for lysine at a position corresponding to amino acid 573 of SEQ ID NO: 1; or
   (vi) arginine substituted for glycine at a position corresponding to amino acid 572 of SEQ ID NO: 1, and tyrosine substituted for lysine at a position corresponding to amino acid 573 of SEQ ID NO: 1; or
(vii) leucine substituted for glutamine at a position corresponding to amino acid 522 of SEQ ID NO: 1, valine substituted for alanine at a position corresponding to amino acid 552 of SEQ ID NO: 1, and arginine substituted for glycine at a position corresponding to amino acid 572 of SEQ ID NO: 1; or
(viii) leucine substituted for glutamine at a position corresponding to amino acid 522 of SEQ ID NO: 1, valine substituted for alanine at a position corresponding to amino acid 552 of SEQ ID NO: 1, and tyrosine substituted for lysine at a position corresponding to amino acid 573 of SEQ ID NO: 1; or
(ix) leucine substituted for glutamine at a position corresponding to amino acid 522 of SEQ ID NO: 1, arginine substituted for glycine at a position corresponding to amino acid 572 of SEQ ID NO: 1, and tyrosine substituted for lysine at a position corresponding to amino acid 573 of SEQ ID NO: 1; or
(x) leucine substituted for glutamine at a position corresponding to amino acid 522 of SEQ ID NO: 1, valine substituted for alanine at position 552 of SEQ ID NO: 1, arginine substituted for glycine at a position corresponding to amino acid 572 of SEQ ID NO: 1, and tyrosine substituted for lysine at a position corresponding to amino acid 573 of SEQ ID NO: 1.

\* \* \* \* \*

SEQUENCE LISTING

<160> NUMBER OF SEQ ID NOS: 6

<210> SEQ ID NO 1
<211> LENGTH: 585
<212> TYPE: PRT
<213> ORGANISM: Homo sapiens

<400> SEQUENCE: 1

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300
```

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 2
<211> LENGTH: 2340
<212> TYPE: PRT
<213> ORGANISM: Homo sapiens

<400> SEQUENCE: 2

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95
```

```
Ala Glu Val Tyr Asp Thr Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510
```

-continued

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys

-continued

```
                930                 935                 940
    Ser Ser Pro Leu Thr Glu Ser Gly Pro Leu Ser Leu Ser Glu Glu
    945                 950                 955                 960

Asn Asn Asp Ser Lys Leu Leu Glu Ser Gly Leu Met Asn Ser Gln Glu
                    965                 970                 975

Ser Ser Trp Gly Lys Asn Val Ser Ser Thr Glu Ser Gly Arg Leu Phe
                980                 985                 990

Lys Gly Lys Arg Ala His Gly Pro Ala Leu Leu Thr Lys Asp Asn Ala
                    995                 1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080

Ser Asn Lys Thr Thr Ser Ser Lys Asn Met Glu Met Val Gln Gln
        1085                1090                1095

Lys Lys Glu Gly Pro Ile Pro Pro Asp Ala Gln Asn Pro Asp Met
        1100                1105                1110

Ser Phe Phe Lys Met Leu Phe Leu Pro Glu Ser Ala Arg Trp Ile
        1115                1120                1125

Gln Arg Thr His Gly Lys Asn Ser Leu Asn Ser Gly Gln Gly Pro
        1130                1135                1140

Ser Pro Lys Gln Leu Val Ser Leu Gly Pro Glu Lys Ser Val Glu
        1145                1150                1155

Gly Gln Asn Phe Leu Ser Glu Lys Asn Lys Val Val Gly Lys
        1160                1165                1170

Gly Glu Phe Thr Lys Asp Val Gly Leu Lys Glu Met Val Phe Pro
        1175                1180                1185

Ser Ser Arg Asn Leu Phe Leu Thr Asn Leu Asp Asn Leu His Glu
        1190                1195                1200

Asn Asn Thr His Asn Gln Glu Lys Lys Ile Gln Glu Glu Ile Glu
        1205                1210                1215

Lys Lys Glu Thr Leu Ile Gln Glu Asn Val Val Leu Pro Gln Ile
        1220                1225                1230

His Thr Val Thr Gly Thr Lys Asn Phe Met Lys Asn Leu Phe Leu
        1235                1240                1245

Leu Ser Thr Arg Gln Asn Val Glu Gly Ser Tyr Asp Gly Ala Tyr
        1250                1255                1260

Ala Pro Val Leu Gln Asp Phe Arg Ser Leu Asn Asp Ser Thr Asn
        1265                1270                1275

Arg Thr Lys Lys His Thr Ala His Phe Ser Lys Lys Gly Glu Glu
        1280                1285                1290

Glu Asn Leu Glu Gly Leu Gly Asn Gln Thr Lys Gln Ile Val Glu
        1295                1300                1305

Lys Tyr Ala Cys Thr Thr Arg Ile Ser Pro Asn Thr Ser Gln Gln
        1310                1315                1320

Asn Phe Val Thr Gln Arg Ser Lys Arg Ala Leu Lys Gln Phe Arg
        1325                1330                1335
```

```
Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725
```

```
Gly Met Ser Ser Ser Pro His Val Leu Arg Asn Arg Ala Gln Ser
    1730            1735                1740

Gly Ser Val Pro Gln Phe Lys Lys Val Val Phe Gln Glu Phe Thr
    1745            1750                1755

Asp Gly Ser Phe Thr Gln Pro Leu Tyr Arg Gly Glu Leu Asn Glu
    1760            1765                1770

His Leu Gly Leu Leu Gly Pro Tyr Ile Arg Ala Glu Val Glu Asp
    1775            1780                1785

Asn Ile Met Val Thr Phe Arg Asn Gln Ala Ser Arg Pro Tyr Ser
    1790            1795                1800

Phe Tyr Ser Ser Leu Ile Ser Tyr Glu Glu Asp Gln Arg Gln Gly
    1805            1810                1815

Ala Glu Pro Arg Lys Asn Phe Val Lys Pro Asn Glu Thr Lys Thr
    1820            1825                1830

Tyr Phe Trp Lys Val Gln His His Met Ala Pro Thr Lys Asp Glu
    1835            1840                1845

Phe Asp Cys Lys Ala Trp Ala Tyr Phe Ser Asp Val Asp Leu Glu
    1850            1855                1860

Lys Asp Val His Ser Gly Leu Ile Gly Pro Leu Leu Val Cys His
    1865            1870                1875

Thr Asn Thr Leu Asn Pro Ala His Gly Arg Gln Val Thr Val Gln
    1880            1885                1890

Glu Phe Ala Leu Phe Phe Thr Ile Phe Asp Glu Thr Lys Ser Trp
    1895            1900                1905

Tyr Phe Thr Glu Asn Met Glu Arg Asn Cys Arg Ala Pro Cys Asn
    1910            1915                1920

Ile Gln Met Glu Asp Pro Thr Phe Lys Glu Asn Tyr Arg Phe His
    1925            1930                1935

Ala Ile Asn Gly Tyr Ile Met Asp Thr Leu Pro Gly Leu Val Met
    1940            1945                1950

Ala Gln Asp Gln Arg Ile Arg Trp Tyr Leu Leu Ser Met Gly Ser
    1955            1960                1965

Asn Glu Asn Ile His Ser Ile His Phe Ser Gly His Val Phe Thr
    1970            1975                1980

Val Arg Lys Lys Glu Glu Tyr Lys Met Ala Leu Tyr Asn Leu Tyr
    1985            1990                1995

Pro Gly Val Phe Glu Thr Val Glu Met Leu Pro Ser Lys Ala Gly
    2000            2005                2010

Ile Trp Arg Val Glu Cys Leu Ile Gly Glu His Leu His Ala Gly
    2015            2020                2025

Met Ser Thr Leu Phe Leu Val Tyr Ser Asn Lys Cys Gln Thr Pro
    2030            2035                2040

Leu Gly Met Ala Ser Gly His Ile Arg Asp Phe Gln Ile Thr Ala
    2045            2050                2055

Ser Gly Gln Tyr Gly Gln Trp Ala Pro Lys Leu Ala Arg Leu His
    2060            2065                2070

Tyr Ser Gly Ser Ile Asn Ala Trp Ser Thr Lys Glu Pro Phe Ser
    2075            2080                2085

Trp Ile Lys Val Asp Leu Leu Ala Pro Met Ile Ile His Gly Ile
    2090            2095                2100

Lys Thr Gln Gly Ala Arg Gln Lys Phe Ser Ser Leu Tyr Ile Ser
    2105            2110                2115

Gln Phe Ile Ile Met Tyr Ser Leu Asp Gly Lys Lys Trp Gln Thr
```

```
                2120                2125                2130
Tyr Arg Gly Asn Ser Thr Gly Thr Leu Met Val Phe Phe Gly Asn
            2135                2140                2145

Val Asp Ser Ser Gly Ile Lys His Asn Ile Phe Asn Pro Pro Ile
        2150                2155                2160

Ile Ala Arg Tyr Ile Arg Leu His Pro Thr His Tyr Ser Ile Arg
        2165                2170                2175

Ser Thr Leu Arg Met Glu Leu Met Gly Cys Asp Leu Asn Ser Cys
        2180                2185                2190

Ser Met Pro Leu Gly Met Glu Ser Lys Ala Ile Ser Asp Ala Gln
        2195                2200                2205

Ile Thr Ala Ser Ser Tyr Phe Thr Asn Met Phe Ala Thr Trp Ser
        2210                2215                2220

Pro Ser Lys Ala Arg Leu His Leu Gln Gly Arg Ser Asn Ala Trp
        2225                2230                2235

Arg Pro Gln Val Asn Asn Pro Lys Glu Trp Leu Gln Val Asp Phe
        2240                2245                2250

Gln Lys Thr Met Lys Val Thr Gly Val Thr Thr Gln Gly Val Lys
        2255                2260                2265

Ser Leu Leu Thr Ser Met Tyr Val Lys Glu Phe Leu Ile Ser Ser
        2270                2275                2280

Ser Gln Asp Gly His Gln Trp Thr Leu Phe Phe Gln Asn Gly Lys
        2285                2290                2295

Val Lys Val Phe Gln Gly Asn Gln Asp Ser Phe Thr Pro Val Val
        2300                2305                2310

Asn Ser Leu Asp Pro Pro Leu Leu Thr Arg Tyr Leu Arg Ile His
        2315                2320                2325

Pro Gln Ser Trp Val His Gln Ile Ala Leu Arg Met
        2330                2335                2340

<210> SEQ ID NO 3
<211> LENGTH: 462
<212> TYPE: PRT
<213> ORGANISM: Homo sapiens

<400> SEQUENCE: 3

Met Gln Arg Val Asn Met Ile Met Ala Glu Ser Pro Ser Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Pro Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140
```

```
Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Pro Thr Glu Ala Glu
                195                 200                 205

Thr Ile Leu Asp Asn Ile Thr Gln Gly Thr Gln Ser Phe Asn Asp Phe
        210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ala Ile Pro His His
290                 295                 300

Asn Tyr Asn Ala Ala Ile Asn Lys Tyr Asn His Asp Ile Ala Leu Leu
305                 310                 315                 320

Glu Leu Asp Glu Pro Leu Val Leu Asn Ser Tyr Val Thr Pro Ile Cys
                325                 330                 335

Ile Ala Asp Lys Glu Tyr Thr Asn Ile Phe Leu Lys Phe Gly Ser Gly
                340                 345                 350

Tyr Val Ser Gly Trp Ala Arg Val Phe His Lys Gly Arg Ser Ala Leu
                355                 360                 365

Val Leu Gln Tyr Leu Arg Val Pro Leu Val Asp Arg Ala Thr Cys Leu
        370                 375                 380

Arg Ser Thr Lys Phe Thr Ile Tyr Asn Asn Met Phe Cys Ala Gly Phe
385                 390                 395                 400

His Glu Gly Gly Arg Asp Ser Cys Gln Gly Asp Ser Gly Gly Pro His
                405                 410                 415

Val Thr Glu Val Glu Gly Thr Ser Phe Leu Thr Gly Ile Ile Ser Trp
                420                 425                 430

Gly Glu Glu Cys Ala Met Lys Gly Lys Tyr Gly Ile Tyr Thr Lys Val
                435                 440                 445

Ser Arg Tyr Val Asn Trp Ile Lys Glu Lys Thr Lys Leu Thr
450                 455                 460

<210> SEQ ID NO 4
<211> LENGTH: 488
<212> TYPE: PRT
<213> ORGANISM: Homo sapiens

<400> SEQUENCE: 4

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Thr Arg Ala Asn Ser Phe Leu Glu Glu Met
            35                  40                  45

Lys Lys Gly His Leu Glu Arg Glu Cys Met Glu Glu Thr Cys Ser Tyr
        50                  55                  60
```

```
Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
            195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
            370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480
```

```
Val Ile Thr Ser Ser Pro Leu Lys
                485

<210> SEQ ID NO 5
<211> LENGTH: 466
<212> TYPE: PRT
<213> ORGANISM: Homo sapiens

<400> SEQUENCE: 5

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
    210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
        275                 280                 285

Ile Ile Pro Ser Thr Tyr Val Pro Gly Thr Thr Asn His Asp Ile Ala
    290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365
```

```
Asp Cys Leu Gln Gln Ser Arg Lys Val Gly Asp Ser Pro Asn Ile Thr
        370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
                405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
        435                 440                 445

Lys Leu Met Arg Ser Glu Pro Arg Pro Gly Val Leu Leu Arg Ala Pro
450                 455                 460

Phe Pro
465

<210> SEQ ID NO 6
<211> LENGTH: 2813
<212> TYPE: PRT
<213> ORGANISM: Homo sapiens

<400> SEQUENCE: 6

Met Ile Pro Ala Arg Phe Ala Gly Val Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
        130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
```

```
                260                 265                 270
Arg Thr Cys Ala Gln Glu Gly Met Val Leu Tyr Gly Trp Thr Asp His
            275                 280                 285
Ser Ala Cys Ser Pro Val Cys Pro Ala Gly Met Glu Tyr Arg Gln Cys
        290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
            340                 345                 350
Ser Gly Lys Arg Tyr Pro Pro Gly Thr Ser Leu Ser Arg Asp Cys Asn
        355                 360                 365
Thr Cys Ile Cys Arg Asn Ser Gln Trp Ile Cys Ser Asn Glu Glu Cys
        370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
            420                 425                 430
Ala Asp Asp Arg Asp Ala Val Cys Thr Arg Ser Val Thr Val Arg Leu
435                 440                 445
Pro Gly Leu His Asn Ser Leu Val Lys Leu Lys His Gly Ala Gly Val
    450                 455                 460
Ala Met Asp Gly Gln Asp Val Gln Leu Pro Leu Leu Lys Gly Asp Leu
465                 470                 475                 480
Arg Ile Gln His Thr Val Thr Ala Ser Val Arg Leu Ser Tyr Gly Glu
                485                 490                 495
Asp Leu Gln Met Asp Trp Asp Gly Arg Gly Arg Leu Leu Val Lys Leu
            500                 505                 510
Ser Pro Val Tyr Ala Gly Lys Thr Cys Gly Leu Cys Gly Asn Tyr Asn
        515                 520                 525
Gly Asn Gln Gly Asp Asp Phe Leu Thr Pro Ser Gly Leu Ala Glu Pro
    530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
                565                 570                 575
Thr Arg Phe Ser Glu Glu Ala Cys Ala Val Leu Thr Ser Pro Thr Phe
            580                 585                 590
Glu Ala Cys His Arg Ala Val Ser Pro Leu Pro Tyr Leu Arg Asn Cys
        595                 600                 605
Arg Tyr Asp Val Cys Ser Cys Ser Asp Gly Arg Glu Cys Leu Cys Gly
        610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
                645                 650                 655
Val Tyr Leu Gln Cys Gly Thr Pro Cys Asn Leu Thr Cys Arg Ser Leu
            660                 665                 670
Ser Tyr Pro Asp Glu Glu Cys Asn Glu Ala Cys Leu Glu Gly Cys Phe
        675                 680                 685
```

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser Asn Leu Gln Val Glu  Glu Asp Pro Val Asp  Phe Gly Asn
    1010                1015                1020

Ser Trp Lys Val Ser Ser Gln  Cys Ala Asp Thr Arg  Lys Val Pro
    1025                1030                1035

Leu Asp Ser Ser Pro Ala Thr  Cys His Asn Asn Ile  Met Lys Gln
    1040                1045                1050

Thr Met Val Asp Ser Ser Cys  Arg Ile Leu Thr Ser  Asp Val Phe
    1055                1060                1065

Gln Asp Cys Asn Lys Leu Val  Asp Pro Glu Pro Tyr  Leu Asp Val
    1070                1075                1080

Cys Ile Tyr Asp Thr Cys Ser  Cys Glu Ser Ile Gly  Asp Cys Ala
    1085                1090                1095

```
Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Thr Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Lys Val Ile Val Ile Pro
    1400                1405                1410

Val Gly Ile Gly Pro His Ala Asn Leu Lys Gln Ile Arg Leu Ile
    1415                1420                1425

Glu Lys Gln Ala Pro Glu Asn Lys Ala Phe Val Leu Ser Ser Val
    1430                1435                1440

Asp Glu Leu Glu Gln Gln Arg Asp Glu Ile Val Ser Tyr Leu Cys
    1445                1450                1455

Asp Leu Ala Pro Glu Ala Pro Pro Pro Thr Leu Pro Pro Asp Met
    1460                1465                1470

Ala Gln Val Thr Val Gly Pro Gly Leu Leu Gly Val Ser Thr Leu
    1475                1480                1485

Gly Pro Lys Arg Asn Ser Met Val Leu Asp Val Ala Phe Val Leu
```

-continued

```
              1490                1495                1500
Glu Gly Ser Asp Lys Ile Gly Glu Ala Asp Phe Asn Arg Ser Lys
              1505                1510                1515
Glu Phe Met Glu Val Ile Gln Arg Met Asp Val Gly Gln Asp
              1520                1525                1530
Ser Ile His Val Thr Val Leu Gln Tyr Ser Tyr Met Val Thr Val
              1535                1540                1545
Glu Tyr Pro Phe Ser Glu Ala Gln Ser Lys Gly Asp Ile Leu Gln
              1550                1555                1560
Arg Val Arg Glu Ile Arg Tyr Gln Gly Gly Asn Arg Thr Asn Thr
              1565                1570                1575
Gly Leu Ala Leu Arg Tyr Leu Ser Asp His Ser Phe Leu Val Ser
              1580                1585                1590
Gln Gly Asp Arg Glu Gln Ala Pro Asn Leu Val Tyr Met Val Thr
              1595                1600                1605
Gly Asn Pro Ala Ser Asp Glu Ile Lys Arg Leu Pro Gly Asp Ile
              1610                1615                1620
Gln Val Val Pro Ile Gly Val Gly Pro Asn Ala Asn Val Gln Glu
              1625                1630                1635
Leu Glu Arg Ile Gly Trp Pro Asn Ala Pro Ile Leu Ile Gln Asp
              1640                1645                1650
Phe Glu Thr Leu Pro Arg Glu Ala Pro Asp Leu Val Leu Gln Arg
              1655                1660                1665
Cys Cys Ser Gly Glu Gly Leu Gln Ile Pro Thr Leu Ser Pro Ala
              1670                1675                1680
Pro Asp Cys Ser Gln Pro Leu Asp Val Ile Leu Leu Leu Asp Gly
              1685                1690                1695
Ser Ser Ser Phe Pro Ala Ser Tyr Phe Asp Glu Met Lys Ser Phe
              1700                1705                1710
Ala Lys Ala Phe Ile Ser Lys Ala Asn Ile Gly Pro Arg Leu Thr
              1715                1720                1725
Gln Val Ser Val Leu Gln Tyr Gly Ser Ile Thr Thr Ile Asp Val
              1730                1735                1740
Pro Trp Asn Val Val Pro Glu Lys Ala His Leu Leu Ser Leu Val
              1745                1750                1755
Asp Val Met Gln Arg Glu Gly Gly Pro Ser Gln Ile Gly Asp Ala
              1760                1765                1770
Leu Gly Phe Ala Val Arg Tyr Leu Thr Ser Glu Met His Gly Ala
              1775                1780                1785
Arg Pro Gly Ala Ser Lys Ala Val Val Ile Leu Val Thr Asp Val
              1790                1795                1800
Ser Val Asp Ser Val Asp Ala Ala Ala Asp Ala Ala Arg Ser Asn
              1805                1810                1815
Arg Val Thr Val Phe Pro Ile Gly Ile Gly Asp Arg Tyr Asp Ala
              1820                1825                1830
Ala Gln Leu Arg Ile Leu Ala Gly Pro Ala Gly Asp Ser Asn Val
              1835                1840                1845
Val Lys Leu Gln Arg Ile Glu Asp Leu Pro Thr Met Val Thr Leu
              1850                1855                1860
Gly Asn Ser Phe Leu His Lys Leu Cys Ser Gly Phe Val Arg Ile
              1865                1870                1875
Cys Met Asp Glu Asp Gly Asn Glu Lys Arg Pro Gly Asp Val Trp
              1880                1885                1890
```

```
Thr Leu Pro Asp Gln Cys His Thr Val Thr Cys Gln Pro Asp Gly
    1895                1900            1905

Gln Thr Leu Leu Lys Ser His Arg Val Asn Cys Asp Arg Gly Leu
    1910                1915            1920

Arg Pro Ser Cys Pro Asn Ser Gln Ser Pro Val Lys Val Glu Glu
    1925                1930            1935

Thr Cys Gly Cys Arg Trp Thr Cys Pro Cys Val Cys Thr Gly Ser
    1940                1945            1950

Ser Thr Arg His Ile Val Thr Phe Asp Gly Gln Asn Phe Lys Leu
    1955                1960            1965

Thr Gly Ser Cys Ser Tyr Val Leu Phe Gln Asn Lys Glu Gln Asp
    1970                1975            1980

Leu Glu Val Ile Leu His Asn Gly Ala Cys Ser Pro Gly Ala Arg
    1985                1990            1995

Gln Gly Cys Met Lys Ser Ile Glu Val Lys His Ser Ala Leu Ser
    2000                2005            2010

Val Glu Leu His Ser Asp Met Glu Val Thr Val Asn Gly Arg Leu
    2015                2020            2025

Val Ser Val Pro Tyr Val Gly Gly Asn Met Glu Val Asn Val Tyr
    2030                2035            2040

Gly Ala Ile Met His Glu Val Arg Phe Asn His Leu Gly His Ile
    2045                2050            2055

Phe Thr Phe Thr Pro Gln Asn Asn Glu Phe Gln Leu Gln Leu Ser
    2060                2065            2070

Pro Lys Thr Phe Ala Ser Lys Thr Tyr Gly Leu Cys Gly Ile Cys
    2075                2080            2085

Asp Glu Asn Gly Ala Asn Asp Phe Met Leu Arg Asp Gly Thr Val
    2090                2095            2100

Thr Thr Asp Trp Lys Thr Leu Val Gln Glu Trp Thr Val Gln Arg
    2105                2110            2115

Pro Gly Gln Thr Cys Gln Pro Ile Leu Glu Glu Gln Cys Leu Val
    2120                2125            2130

Pro Asp Ser Ser His Cys Gln Val Leu Leu Leu Pro Leu Phe Ala
    2135                2140            2145

Glu Cys His Lys Val Leu Ala Pro Ala Thr Phe Tyr Ala Ile Cys
    2150                2155            2160

Gln Gln Asp Ser Cys His Gln Glu Gln Val Cys Glu Val Ile Ala
    2165                2170            2175

Ser Tyr Ala His Leu Cys Arg Thr Asn Gly Val Cys Val Asp Trp
    2180                2185            2190

Arg Thr Pro Asp Phe Cys Ala Met Ser Cys Pro Pro Ser Leu Val
    2195                2200            2205

Tyr Asn His Cys Glu His Gly Cys Pro Arg His Cys Asp Gly Asn
    2210                2215            2220

Val Ser Ser Cys Gly Asp His Pro Ser Glu Gly Cys Phe Cys Pro
    2225                2230            2235

Pro Asp Lys Val Met Leu Glu Gly Ser Cys Val Pro Glu Glu Ala
    2240                2245            2250

Cys Thr Gln Cys Ile Gly Glu Asp Gly Val Gln His Gln Phe Leu
    2255                2260            2265

Glu Ala Trp Val Pro Asp His Gln Pro Cys Gln Ile Cys Thr Cys
    2270                2275            2280
```

```
Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
```

```
             2675                2680                2685
Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810
```